(12) United States Patent
Jen et al.

(10) Patent No.: US 9,214,574 B2
(45) Date of Patent: Dec. 15, 2015

(54) FULLERENE SURFACTANTS AND THEIR USE IN POLYMER SOLAR CELLS

(71) Applicant: University of Washington through its Center for Commercialization, Seattle, WA (US)

(72) Inventors: Kwan-Yue Jen, Kenmore, WA (US); Hin-Lap Yip, Seattle, WA (US); Chang-zhi Li, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 437 days.

(21) Appl. No.: 13/706,230

(22) Filed: Dec. 5, 2012

(65) Prior Publication Data

US 2013/0160827 A1 Jun. 27, 2013

Related U.S. Application Data

(60) Provisional application No. 61/566,943, filed on Dec. 5, 2011.

(51) Int. Cl.
| | |
|---|---|
| *H01L 31/0216* | (2014.01) |
| *C07D 207/08* | (2006.01) |
| *C07D 209/70* | (2006.01) |
| *B82Y 10/00* | (2011.01) |
| *H01L 51/00* | (2006.01) |
| *H01L 51/42* | (2006.01) |

(52) U.S. Cl.
CPC ........... *H01L 31/02167* (2013.01); *B82Y 10/00* (2013.01); *C07D 207/08* (2013.01); *C07D 209/70* (2013.01); *H01L 51/0047* (2013.01); *H01L 51/0036* (2013.01); *H01L 51/0043* (2013.01); *H01L 51/4253* (2013.01); *Y02E 10/549* (2013.01)

(58) Field of Classification Search
CPC ......................... H01L 31/02167; C07D 207/08
See application file for complete search history.

(56) References Cited

U.S. PATENT DOCUMENTS

| | | |
|---|---|---|
| 2004/0054151 A1 | 3/2004 | Dorn |
| 2009/0188558 A1 | 7/2009 | Jen |
| 2011/0132439 A1 | 6/2011 | Jen |
| 2013/0160827 A1 | 6/2013 | Jen |

FOREIGN PATENT DOCUMENTS

| | | |
|---|---|---|
| JP | 2009-057356 A | 3/2009 |
| WO | 2012/156723 A1 | 11/2012 |
| WO | 2013/006095 A1 | 1/2013 |

OTHER PUBLICATIONS

Li et al., "Nanoscale Cavities for Fulleropyrrolidinium in Nafion Membrane," Chem. Mater. 2003, 15, 4739-4744.*
Li, F., et al., "Acridine Orange Base as a Dopant for n Doping of C60 Thin Films," Journal of Applied Physics 100:023716-1-023716-9, Jul. 2006.

(Continued)

*Primary Examiner* — Ling Choi
*Assistant Examiner* — Catherine S Branch
(74) *Attorney, Agent, or Firm* — Christensen O'Connor Johnson Kindness PLLC

(57) ABSTRACT

Fullerene surfactant compounds useful as interfacial layer in polymer solar cells to enhance solar cell efficiency. Polymer solar cell including a fullerene surfactant-containing interfacial layer intermediate cathode and active layer.

13 Claims, 16 Drawing Sheets

(56) References Cited

OTHER PUBLICATIONS

Li, F.H., et al., "Leuco Crystal Violet as a Dopant for n-Doping of Organic Thin Films of Fullerene C60," Journal of Physical Chemistry B 108(44):17076-17082, Nov. 2004.

Li, G., et al., "High-Efficiency Solution Processable Polymer Photovoltaic Cells by Self-Organization of Polymer Blends," Nature: Materials 4(11):864-868, Nov. 2005.

Li, H., et al., "Multifunctional, Polymorphic, Ionic Fullerene Supramolecular Materials: Self-Assembly and Thermotropic Properties," Langmuir, 27(12):7493-7501, Jun. 2011.

Li, J., et al., "Dynamical Simulation of Photoinduced Electron Transfer Reactions in Dye-Semiconductor Systems With Different Anchor Groups," Journal of Physical Chemistry C 112(32):12326-12333, Aug. 2008.

Li, Y.F. and Y.P. Zou, "Conjugated Polymer Photovoltaic Materials With Broad Absorption Band and High Charge Carrier Mobility," Advanced Materials 20(15):2952-2958, Aug. 2008.

Liang, Y., et al., "Development of New Semiconducting Polymers for High Performance Solar Cells," Journal of the American Chemical Society 131(1):56-57, Jan. 2009.

Liang, Y., et al., "For the Bright Future—Bulk Heterojunction Polymer Solar Cells With Power Conversion Efficiency of 7.4%," Advanced Materials 22(20):E135-E138, May 2010.

Liang, Y., et al., "Highly Efficient Solar Cell Polymers Developed Via Fine-Tuning of Structural and Electronic Properties," Journal of the American Chemical Society 131(22):7792-7799, Jun. 2009.

Liu, M., et al., "Efficient Planar Heterojunction Perovskite Solar Cells by Vapour Deposition," Nature 501(7467):395-398, Sep. 2013, [with Methods, Extended Data Figures and Extended Data Tables, 3 pages].

Lloyd, M.T., et al., "Impact of Contact Evolution on the Shelf Life of Organic Solar Cells," Journal of Materials Chemistry 19(41):7638-7642, Nov. 2009.

Luo, J., et al., "Enhanced Open-Circuit Voltage in Polymer Solar Cells," Applied Physics Letters 95(4):043301-1-043301-3, Jul. 2009.

Ma, et al., "Interface Engineering for Organic Electronics," Advanced Functional Materials 20(9):1371-1388, May 2010.

Ma, H., et al., "Multifunctional Phosphonic Acid Self-Assembled Monolayers on Metal Oxides as Dielectrics, Interface Modification Layers and Semiconductors for Low-Voltage High-Performance Organic Field-Effect Transistors," Physical Chemistry Chemical Physics 14(41):14110-14126, Oct. 2012.

Ma, W.L., et al., "Thermally Stable, Efficient Polymer Solar Cells With Nanoscale Control of the Interpenetrating Network Morphology," Advanced Functional Materials 15(10):1617-1622, Oct. 2005.

Maennig, B., et al., "Controlled p-type Doping of Polycrystalline and Amorphous Organic Layers: Self-Consistent Description of Conductivity and Field-Effect Mobility by a Microscopic Percolation Model," Physical Review B 64(19):195208-1-195208-9, Nov. 2001.

Marczak, R., et al., "Communication via Electron and Energy Transfer between Zinc Oxide Nanoparticles and Organic Adsorbates," Journal of Physical Chemistry C 113(11):4669-4678, Mar. 2009.

Matsumoto, F., et al., "Synthesis of Thienyl Analogues of PCBM and Investigation of Morphology of Mixtures in P3HT," Beilstein Journal of Organic Chemistry 4:33, 2008, pp. 1-6.

McNeill, C.R., et al., "Dual Electron Donor/Electron Acceptor Character of a Conjugated Polymer in Efficient Photovoltaic Diodes," Applied Physics Letters 90(19):193506-1-193506-3, May 2007.

Meerheim, R., et al., "Efficiency and Stability of p-i-n Type Organic Light Emitting Diodes for Display and Lighting Applications," Proceedings of the IEEE 97(9):1606-1626, Sep. 2009.

Melby, L.R., et al., "Substituted Quinodimethans. II. Anion-radical Derivatives and Complexes of 7,7,8,8-Tetracyanoquinodimethan," Journal of the American Chemical Society 84(17):3374-3387, Sep. 1962.

Menke, T., et al., "In-Situ Conductivity and Seebeck Measurements of Highly Efficient N-Dopants in Fullerene $C_{60}$," Applied Physics Letters 100(9):093304-1-093304-4, Feb. 2012.

Mihailetchi, V.D., et al., "Cathode Dependence of the Open-Circuit Voltage of Polymer:Fullerene Bulk Heterojunction Solar Cells," Journal of Applied Physics 94(10):6849-6854, Nov. 2003.

Mitzi, D.B., et al., "Conducting Layered Organic-Inorganic Halides Containing <110>-Oriented Perovskite Sheets," Science 267(5203):1473-1476, Mar. 1995.

Montalti, M., et al., "Luminescent Ruthenium(II) Bipyridyl-Phosphonic Acid Complexes: pH Dependent Photophysical Behavior and Quenching With Divalent Metal Ions," Inorganic Chemistry 39(1):76-84, Jan. 2000.

Mor, G.K., et al., "Visible to Near-Infrared Light Harvesting in $TiO_2$ Nanotube Array-P3HT Based Heterojunction Solar Cells," Nano Letters 9(12):4250-4257, Dec. 2009.

Moser, J., et al., "Surface Complexation of Colloidal Semiconductors Strongly Enhances Interfacial Electron-Transfer Rates," Langmuir 7(12):3012-3018, Dec. 1991.

Nakamura, E., and H. Isobe, "Functionalized Fullerenes in Water. The First 10 Years of Their Chemistry Biology, and Nanoscience," Accounts of Chemical Research 36(11):807-815, Nov. 2003.

Nelson, J. "Continuous-Time Random-Walk Model of Electron Transport in Nanocrystalline $TiO_2$ Electrodes," Physical Review B 59(23):15374-15380, Jun. 1999.

Nielsen, C.B., et al., "Synthesis and Characterization of Water-Soluble Phenylene-Vinylene-Based Singlet Oxygen Sensitizers for Two-Photon Excitation," Journal of Organic Chemistry 70(18):7065-7079, Sep. 2005.

Niu, Y.-H., et al., "Thermally Crosslinked Hole-Transporting Layers for Cascade Hole-Injection and Effective Electron-Blocking/Exciton-Confinement in Phosphorescent Polymer Light-Emitting Diodes," Applied Physics Letters 88(9):093505-1-093505-3, Feb. 2006.

Nollau, A., et al., "Controlled n-type Doping of a Molecular Organic Semiconductor: Naphthalenetetracarboxylic dianhydride (NTCDA) Doped With bis(ethylenedithio)-tetrathiafulvalene (BEDT-TTF)," Journal of Applied Physics 87(9):4340-4343, May 2000.

Oh, J.H., et al., "Molecular n-type Doping for Air-Stable Electron Transport in Vacuum-Processed n-Channel Organic Transistors," Applied Physics Letters 97:243305-1-243305-3, 2010.

Oh, S.-H., et al., "Novel Cationic Water-Soluble Polyfluorene Derivatives With Ion-Transporting Side Groups for Efficient Electron Injection in PLEDs," Organic Electronics 8(6):773-783, Dec. 2007.

Oh, S.-H., et al., "Water-Soluble Polyfluorenes as an Interfacial Layer Leading to Cathode-Independent High Performance of Organic Solar Cells," Advanced Functional Materials 20(12):1977-1983, Dec. 2010.

O'Malley, K.M., et al., "Enhanced Open-Circuit Voltage in High Performance Polymer/Fullerene Bulk-Heterojunction Solar Cells by Cathode Modification With a C60 Surfactant," Advanced Energy Materials 2(1):82-86, Jan. 2012.

O'Regan, B. and M. Gratzel, "A Low-Cost, High-Efficiency Solar Cell Based on Dye-Sensitized Colloidal $TiO_2$ Films," Nature 353(6346):737-740, Oct. 1991.

O'Regan, O., and F. Lenzmann, "Charge Transport and Recombination in a Nanoscale Interpenetrating Network of n-Type and p-Type Semiconductors: Transient Photocurrent and Photovoltage Studies of $TiO_2$/Dye/CuSCN Photovoltaic Cells," Journal of Physical Chemistry B 108(14):4342-4350, Apr. 2004.

Park, S.H., et al., "Bulk Heterojunction Solar Cells With Internal Quantum Efficiency Approaching 100%," Nature: Photonics 3(5):297-303, May 2009.

Peet, J., et al., "Efficiency Enhancement in Low-Bandgap Polymer Solar Cells by Processing With Alkane Dithiols," Nature: Materials 6(7):497-500, Jul. 2007.

Persson, P., et al., "Quantum Chemical Study of Photoinjection Processes in Dye-Sensitized $TiO_2$ Nanoparticles," Journal of Physical Chemistry B 104(44):10348-10351, Nov. 2000.

Petrozza, A., et al., "Electron Transport and Recombination in Dye-Sensitized Mesoporous $TiO_2$ Probed by Photoinduced Charge-Conductivity Modulation Spectroscopy With Monte Carlo Modeling," Journal of the American Chemical Society 130(39):12912-12920, Oct. 2008.

(56) References Cited

OTHER PUBLICATIONS

Pfeiffer, M., et al., "Doped Organic Semiconductors: Physics and Application in Light Emitting Diodes," Organic Electronics 4(2-3):89-103, Sep. 2003.
Po, et al., "The Role of Buffer Layers in Polymer Solar Cells," Energy & Environmental Science 4(2):285-310, Feb. 2011.
Qi, Y., et al., "Solution Doping of Organic Semiconductors Using Air-Stable n-Dopants," Applied Physics Letters 100(8):083305-1-083305-4, Feb. 2012.
Qin, R., et al., "A Planar Copolymer for High Efficiency Polymer Solar Cells," Journal of the American Chemical Society, 131(41):14612-14613, Oct. 2009.
Ramakrishna, G., et al., "Dynamics of Back-Electron Transfer Processes of Strongly Coupled Triphenyl Methane Dyes Adsorbed on TiO2 Nanoparticle Surface as Studied by Fast and Ultrafast Visible Spectroscopy," Journal of Physical Chemistry B 105(51):12786-12796, Dec. 2001.
Reddy, P.Y., et al., "Efficient Sensitization of Nanocrystalline $TiO_2$ Films by a Near-IR-Absorbing Unsymmetrical Zinc Phthalocyanine," Angewandte Chemie International Edition 46(3):373-376, Jan. 2007.
Reese, M.O., et al., "Optimal Negative Electrodes for Poly(3-hexylthiophene): [6,6]-phenyl C61-butyric Acid Methyl Ester Bulk Heterojunction Photovoltaic Devices," Applied Physics Letters 92(5):053307-1-053307-3, Feb. 2008, 3 pages.
Rodríguez, R., et al., "Surface Complexation at the $TiO_2$ (anatase)/Aqueous Solution Interface: Chemisorption of Catechol," Journal of Colloid and Interface Science 177(1):122-131, Jan. 1996.
Roest, A.L., et al., "Staircase in the Electron Mobility of a ZnO Quantum Dot Assembly due to Shell Filling," Physical Review Letters 89(3):036801-1-036801-4, Jul. 2002.
Ross, R., et al., "Endohedral Fullerenes for Organic Photovoltaic Devices," Nature: Materials 8(3):208-212, Mar. 2009.
Rothenberger, G., et al., "Spectroscopy of Conduction Band Electrons in Transparent Metal Oxide Semiconductor Films: Optical Determination of the Flatband Potential of Colloidal Titanium Dioxide Films," Journal of Physical Chemistry 96(14):5983-5986, Jul. 1992.
Rouquerol, J., et al., "Recommendations for the Characterization of Porous Solids," Pure and Applied Chemistry 66(8):1739-1758, Jan. 1994.
Sariciftci, N.S., et al., "Photoinduced Electron Transfer From a Conducting Polymer to Buckminsterfullerene," Science 258(5087):1474-1476, Nov. 1992.
Schlaf, R., et al., "Work Function Measurements on Indium Tin Oxide Films," Journal of Electron Spectroscopy and Related Phenomena 120(1-3):149-154, Oct. 2001.
Seah, M.P., "Summary of ISO/TC 201 Standard: VII ISO 15472:2001—Surface Chemical Analysis—X-Ray Photoelectron Spectrometers—Calibration of Energy Scales," Surface and Interface Analysis, 31:721-723, Aug. 2001.
Seo, J.H., et al., "Improved Injection in n-Type Organic Transistors With Conjugated Polyelectrolytes," Journal of the American Chemical Society 131(51):18220-18221, Dec. 2009.
Shaheen, S.E., et al., "2.5% Efficient Organic Plastic Solar Cells," Applied Physics Letters 78(6):841-843, Feb. 2001.
Sing, K.S.W., et al., "Reporting Physisorption Data for Gas/Solid Systems With Special Reference to the Determination of Surface Area and Porosity (Recommendations 1984)," Pure and Applied Chemistry 57(4):603-619, Jan. 1985.
Snaith, H.J., and M. Grätzel, "Enhanced Charge Mobility in a Molecular Hole Transporter Via Addition of Redox Inactive Ionic Dopant: Implication to Dye-Sensitized Solar Cells," Applied Physics Letters 89(26):262114-1-262114-3, Dec. 2006.
Snaith, H.J., et al., "High Extinction Coefficient "Antenna" Dye in Solid-State Dye-Sensitized Solar Cells: A Photophysical and Electronic Study," Journal of Physical Chemistry C 112(20):7562-7566, May 2008.
Snaith, H.J., et al., "Ion-Coordinating Sensitizer in Solid-State Hybrid Solar Cells," Angewandte Chemie International Edition 44(39):6413-6417, Oct. 2005.
Steim, R., et al., "Interface Materials for Organic Solar Cells," Journal of Materials Chemistry 20(13):2499-2512, Apr. 2010.
Stephens, P.J., et al., "Ab Initio Calculation of Vibrational Absorption and Circular Dichroism Spectra Using Density Functional Force Fields," Journal of Physical Chemistry 98(45):11623-11627, Feb. 1994.
Suemori, K., et al., "Electrical Shorting of Organic Photovoltaic Films Resulting From Metal Migration," Journal of Applied Physics 99:036109-1-036109-3, 2006.
Sun, D., et al., "Reversible Interchange of Charge-Transfer Versus Electron-Transfer States in Organic Electron Transfer via Cross-Exchanges Between Diamagnetic (Donor/Acceptor) Dyads," Journal of Physical Chemistry B 111(24):6655-6666, Feb. 2007.
Tae, E.L., et al., "A Strategy to Increase the Efficiency of the Dye-Sensitized $TiO_2$ Solar Cells Operated by Photoexcitation of Dye-to-$TiO_2$ Charge-Transfer Bands," Journal of Physical Chemistry B 109(47):22513-22522, Dec. 2005.
Tai, Q., et al., "Enhanced Photovoltaic Performance of Polymer Solar Cells by Adding Fullerene End-Capped Polyethylene Glycol," Journal of Materials Chemistry 21(19):6848-6853, May 2011.
Takanezawa, K., et al., "Efficiency Enhancement of Polymer Photovoltaic Devices Hybridized With ZnO Nanorod Arrays by the Introduction of a Vanadium Oxide Buffer Layer," Applied Physics Letters 93(6):063308-1-063308-3, Aug. 2008.
Tanaka, S., et al., "Doping Effect of Tetrathianaphthacene Molecule in Organic Semiconductors on Their Interfacial Electronic Structures Studied by UV Photoemission Spectroscopy," Japanese Journal of Applied Physics 44(6A):3760-3763, Jun. 2005.
Thompson, B.C. and J.M.J. Frechet, "Polymer-Fullerene Composite Solar Cells," Angewandte Chemie International Edition, 47(1):58-77, Dec. 2008.
Ting, G.G., II, et al "Study on the Formation of Self-Assembled Monolayers on Sol-Gel Processed Hafnium Oxide as Dielectric Layers," Langmuir 25(4):2140-2147, Feb. 2009.
Vandewal, K., et al., "On the Origin of the Open-Circuit Voltage of Polymer-Fullerene Solar Cells," Nature: Materials 8(11):904-909, Nov. 2009.
Vaynzof, Y., et al., "Improved Photoinduced Charge Carriers Separation in Organic-Inorganic Hybrid Photovoltaic Devices," Applied Physics Letters 97(3):033309-1-033309-3, Jul. 2010.
Walzer, K., et al., "Highly Efficient Organic Devices Based on Electrically Doped Transport Layers," Chemical Reviews 107(4):1233-1271, Apr. 2007.
Wang, C., et al., "Semiconducting π -Conjugated Systems in Field-Effect Transistors: A Material Odyssey of Organic Electronics," Chemical Reviews 112(4):2208-2267, Apr. 2011.
Wang, P., et al., "A Stable Quasi-Solid-State Dye-Sensitized Solar Cell With an Amphiphilic Ruthenium Sensitizer and Polymer Gel Electrolyte," Nature Materials 2(6):402-407 (Erratum: 2:498), Jun. 2003.
Wei, P., et al., "2-(2-Methoxyphenyl)-1,3-dimethyl-1H-benzoimidazol-3-ium Iodide as a New Air-Stable n-Type Dopant for Vacuum-Processed Organic Semiconductor Thin Films," Journal of the American Chemical Society 134(9):3999-4002, Mar. 2012.
Wei, P., et al., "Use of a 1H-Benzoimidazole Derivative as an n-Type Dopant and to Enable Air-Stable Solution-Processed n-Channel Organic Thin-Film Transistors," Journal of the American Chemical Society 132(26):8852-8853, Jul. 2010.
Wei, Q.S., et al., "Self-Organized Buffer Layers in Organic Solar Cells," Advanced Materials 20(11):2211-2216, Jun. 2008. (Correction noted in Advanced Materials 20(12):2250, 2008.).
Werner, A., et al., "n-Type Doping of Organic Thin Films Using Cationic Dyes," Advanced Functional Materials 14(3):255-260, Mar. 2004.
Werner, A.G., et al., "Pyronin B as a Donor for n-Type Doping of Organic Thin Films," Applied Physics Letters 82(25):4495-4497, Jun. 2003.
Wong, W.Y., et al., "Metallated Conjugated Polymers as a New Avenue Towards High-Efficiency Polymer Solar Cells," Nature Materials 6(7):521-527, Jul. 2007.

(56) References Cited

OTHER PUBLICATIONS

Xu, Z., et al., "Vertical Phase Separation in Poly(3-hexylthiophene): Fullerene Derivative Blends and its Advantage for Inverted Structure Solar Cells," Advanced Functional Materials 19(8):1227-1234, Apr. 2009.

Yamagishi, M., et al., "Air-Stable n-Channel Single-Crystal Transistors With Negligible Threshold Gate Voltage," Applied Physics Letters 94(5):053305-1-053305-3, Feb. 2009.

Yang, C., et al., "Functionalized Methanofullerenes Used as n-Type Materials in Bulk-Heterojunction Polymer Solar Cells and in Field-Effect Transistors," Journal of the American Chemical Society 130(20):6444-6450, May 2008.

Yip, H.-L., et al., "Polymer Solar Cells That Use Self-Assembled-Monolayer- Modified ZnO/Metals as Cathodes," Advanced Materials 20(12):2376-2382, Jun. 2008.

Yip, H.-L., et al., "Self-Assembled Monolayer Modified ZnO/Metal Bilayer Cathodes for Polymer/Fullerene Bulk-Heterojunction Solar Cells," Applied Physics Letters 92(19):193313-1-193313-3, May 2008.

Yu, G., et al., "Polymer Photovoltaic Cells: Enhanced Efficiencies Via a Network of Internal Donor-Acceptor Heterojunctions," Science 270(5243):1789-1791, Dec. 1995.

Zaban, A., et al., "Determination of the Electron Lifetime in Nanocrystalline Dye Solar Cells by Open-Circuit Voltage Decay Measurements," ChemPhysChem 4(8):859-864, Aug. 2003.

Zakeeruddin, S.M., et al., "Molecular Engineering of Photosensitizers for Nanocrystalline Solar Cells: Synthesis and Characterization of Ru Dyes Based on Phosphonated Terpyridines," Inorganic Chemistry 36(25):5937-5946, Dec. 1997.

Zhang, F., et al., "Enhancing the Photovoltage of Polymer Solar Cells by Using a Modified Cathode," Advanced Materials 19(14):1835-1838, Jul. 2007.

Zhang, Y., et al., "A Simple and Effective Way of Achieving Highly Efficient and Thermally Stable Bulk-Heterojunction Polymer Solar Cells Using Amorphous Fullerene Derivatives as Electron Acceptor," Chemistry of Materials 21(13):2598-2600, Jul. 2009 [with Supporting Information, 12 pages].

Zhang, Y., et al., "Indacenodithiophene and Quinoxaline-Based Conjugated Polymers for Highly Efficient Polymer Solar Cells," Chemistry of Materials 23(9)2289-2291, May 2011.

Zhao, Y., et al., "Enhanced Charge Collection in Polymer Photovoltaic Cells by Using an Ethanol-Soluble Conjugated Polyfluorene as Cathode Buffer Layer," Solar Energy Materials and Solar Cells 93(5):604-608, May 2009.

Zheng, L.P., et al., "Methanofullerenes Used as Electron Acceptors in Polymer Photovoltaic Devices," Journal of Physical Chemistry B 108(32):11921-11926, Aug. 2004.

Abrusci, A., et al., "Facile Infiltration of Semiconducting Polymer Into Mesoporous Electrodes for Hybrid Solar Cells," Energy and Environmental Science 4(8):3051-3058, Aug. 2011.

Abrusci, A., et al., "High-Performance Perovskite-Polymer Hybrid Solar Cells via Electronic Coupling With Fullerene Monolayers," Nano Letters 13(7):3124-3128, Jul. 2013.

Anthopoulos, T.D., et al., "High Performance n-Channel Organic Field-Effect Transistors and Ring Oscillators Based on C60 Fullerene Films," Applied Physics Letters 89(21):213504-1-213504-3, Nov. 2006.

Backer, S.A., et al., "High Efficiency Organic Photovoltaics Incorporating a New Family of Soluble Fullerene Derivatives," Chemistry of Materials 19(12):2927-2929, Jun. 2007.

Bardecker, J.A., et al., "Self-Assembled Electroactive Phosphonic Acids on ITO: Maximizing Hole-Injection in Polymer Light-Emitting Diodes," Advanced Functional Materials 18(24):3964-3971, Dec. 2008.

Becke, A.D., "Density-Functional Thermochemistry. III. The Role of Exact Exchange," Journal of Chemical Physics 98(7):5648-5652, Apr. 1993.

Beek, W.J.E., et al., "Hybrid Zinc Oxide Conjugated Polymer Bulk Heterojunction Solar Cells," Journal of Physical Chemistry B 109(19):9505-9516, May 2005.

Beerbom, M.M., et al., "Direct Comparison of Photoemission Spectroscopy and in Situ Kelvin Probe Work Function Measurements on Indium Tin Oxide Films," Journal of Electron Spectroscopy and Related Phenomena 152(1-2):12-17, Jun. 2006.

Bisquert, J., and G. Garcia-Belmonte, "On Voltage, Photovoltage, and Photocurrent in Bulk Heterojunction Organic Solar Cells," Journal of Physical Chemistry Letters 2(15):1950-1964, Aug. 2011.

Bisquert, J., et al., "Electron Lifetime in Dye-Sensitized Solar Cells: Theory and Interpretation of Measurements," Journal of Physical Chemistry C 113(40):17278-17290, Oct. 2009.

Boix, P.P., et al., "Open-Circuit Voltage Limitation in Low-Bandgap Diketopyrrolopyrrole-Based Polymer Solar Cells Processed From Different Solvents," Journal of Physical Chemistry C 115(30):15075-15080, Aug. 2011.

Boix, P.P., et al., "Role of ZnO Electron-Selective Layers in Regular and Inverted Bulk Heterojunction Solar Cells," Journal of Physical Chemistry Letters 2(5):407-411, Mar. 2011.

Borgias, B.A., et al., "Synthetic, Structural, and Physical Studies of Titanium Complexes of Catechol and 3,5-di-tert-butylcatechol," Inorganic Chemistry 23(8):1009-1016, Apr. 1984.

Bosi, S., et al., "Synthesis and Water Solubility of Novel Fullerene Bisadduct Derivatives," European Journal of Organic Chemistry 2003(24):4741-4747, Dec. 2003.

Brabec, C.J., "Semiconductor Aspects of Organic Bulk Heterojunction Solar Cells," in C.J. Brabec et al. (eds.), "Organic Photovoltaics: Concepts and Realization," Springer-Verlag, Berlin, 2003, vol. 60, pp. 159-248.

Brabec, C.J., et al., "Effect of LiF/Metal Electrodes on the Performance of Plastic Solar Cells," Applied Physics Letters 80(7):1288-1290, Feb. 2002.

Brabec, C.J., et al., "Plastic Solar Cells," Advanced Functional Materials 11(1):15-26, Feb. 2001.

Braun, S., et al., "Energy-Level Alignment at Organic/Metal and Organic/Organic Interfaces," Advanced Materials 21(14-15):1450-1472, Apr. 2009.

Burke, A., et al., "A Novel Blue Dye for Near-IR 'Dye-Sensitised' Solar Cell Applications," Chemical Communications 2007(3):234-236, Jan. 2007.

Carano, M., et al., "Modulation of the Reduction Potentials of Fullerene Derivatives," Journal of the American Chemical Society 125(23):7139-7144, Jun. 2003.

Chan, C.K., et al., "Decamethylcobaltocene as an Efficient n-dopant in Organic Electronic Materials and Devices," Organic Electronics 9(5):575-581, Oct. 2008.

Chan, C.K., et al., "Molecular n-Type Doping of 1,4,5,8-Naphthalene Tetracarboxylic Dianhydride by PyroninB Studied Using Direct and Inverse Photoelectron Spectroscopies," Advanced Functional Materials 16(6):831-837, Apr. 2006.

Chan, C.K., et al., "N-type Doping of an Electron-Transport Material by Controlled Gas-Phase Incorporation of Cobaltocene," Chemical Physics Letters 431(1-3):67-71, Nov. 2006.

Chen, F.-C., and S.-C. Chien, "Nanoscale Functional Interlayers Formed Through Spontaneous Vertical Phase Separation in Polymer Photovoltaic Devices," Journal of Materials Chemistry 19(37):6865-6869, Oct. 2009.

Chen, H.-Y., et al., "Polymer Solar Cells With Enhanced Open-Circuit Voltage and Efficiency," Nature: Photonics 3(11):649-653, Nov. 2009.

Chen, K.-S., et al., "Highly Efficient Indacenodithiophene-Based Polymeric Solar Cells in Conventional and Inverted Device Configurations," Organic Electronics 12(5):794-801, May 2011.

Chen, L., et al., "Interface Investigation and Engineering—Achieving High Performance Polymer Photovoltaic Devices," Journal of Materials Chemistry 20(13):2575-2598, Apr. 2010.

Chen, Y.-C., et al., "Low-Bandgap Conjugated Polymer for High Efficient Photovoltaic Applications," Chemical Communications 46(35):6503-6505, Sep. 2010.

Cheng, Y.-J., et al., "Combination of Indene-C60 Bis-Adduct and Cross-Linked Fullerene Interlayer Leading to Highly Efficient Inverted Polymer Solar Cells," Journal of the American Chemical Society 132(49):17381-17383, Dec. 2010.

(56) References Cited

OTHER PUBLICATIONS

Cho, N., et al., "In-situ Crosslinking and n-Doping of Semiconducting Polymers and Their Application as Efficient Electron-Transporting Materials in Inverted Polymer Solar Cells," Advanced Energy Materials 1(6):1148-1153, Nov. 2011.
Cho, N., et al., "n-Doping of Thermally Polymerizable Fullerenes as an Electron Transporting Layer for Inverted Polymer Solar Cells," Journal of Materials Chemistry 21(19):6956-6961, May 2011.
Chou, T.P., et al., "Effects of Dye Loading Conditions on the Energy Conversion Efficiency of ZnO and $TiO_2$ Dye-Sensitized Solar Cells," Journal of Physical Chemistry C 111(50):18804-18811, Dec. 2007.
Chua, L.L., et al., "General Observation of n-Type Field-Effect Behaviour in Organic Semiconductors," Nature 434(7030):194-199, Mar. 2005.
Coakley, K.M., and M.D. McGehee, "Conjugated Polymer Photovoltaic Cells," Chemistry of Materials 16(23):4533-4542, 2004.
"Conductive Polymers," Clevios Downloads, <http://clevios.com/en/downloads/heraeus-conductive-polymers-downloads.aspx> [retrieved May 12, 2015], 3 pages.
Cravino, A., "Origin of the Open Circuit Voltage of Donor-Acceptor Solar Cells: Do Polaronic Energy Levels Play a Role?" Applied Physics Letters 91(24):243502.1-243502.3, Dec. 2007, 3 pages.
Cravino, A., et al., "Characterization of Organic Solar Cells: The Importance of Device Layout," Advanced Functional Materials 17(18):3906-3910, Dec. 2007.
De Jong, M.P., et al., "Stability of the Interface Between Indium-Tin-Oxide and Poly(3,4-ethylenedioxythiophene)/poly (styrenesulfonate) in Polymer Light-Emitting Diodes," Applied Physics Letters 77(14):2255-2257, Oct. 2000.
Dennler, G., et al., "Polymer-Fullerene Bulk-Heterojunction Solar Cells," Advanced Materials 21(13):1323-1338, Apr. 2009.
Docampo, P., et al., "Efficient Organometal Trihalide Perovskite Planar-Heterojunction Solar Cells on Flexible Polymer Substrates," Nature: Communications 4:2761, Nov. 2013, 6 pages.
Dreschel, J., et al., "Efficient Organic Solar Cells Based on a Double p-i-n Architecture Using Doped Wide-Gap Transport Layers," Applied Physics Letters 86(24):244102-1-244102-3, Jun. 2005.
Duarte, A., et al., "Recent Advances in Conjugated Polyelectrolytes for Emerging Optoelectronic Applications," Chemistry of Materials 23(3):501-515, Feb. 2011.
Eperon, G.E., et al., "Morphological Control for High Performance, Solution-Processed Planar Heterojunction Perovskite Solar Cells," Advanced Functional Materials 24(1):151-157, Jan. 2014.
Eperon, G.E., et al., "Neutral Color Semitransparent Microstructured Perovskite Solar Cells," ACS Nano 8(1):591-598, Jan. 2014.
Ernstorfer, R., et al., "Role of Molecular Anchor Groups in Molecule-to-Semiconductor Electron Transfer," Journal of Physical Chemistry B 110(50):25383-25391, Dec. 2006.
Etgar, L., et al., "Mesoscopic $CH_3NH_3PbI_3/TiO_2$ Heterojunction Solar Cells," Journal of the American Chemical Society 134(42):17396-17399, Oct. 2012.
Gao, Y., et al., "Surface Doping of Conjugated Polymers by Graphene Oxide and Its Application for Organic Electronic Devices," Advanced Materials 23(16):1903-1908, Apr. 2011.
Garcia-Belmonte, G., and J. Bisquert, "Open-Circuit Voltage Limit Caused by Recombination Through Tail States in Bulk Heterojunction Polymer-Fullerene Solar Cells," Applied Physics Letters 96(11):113301-1-113301-3, Mar. 2010.
Garcia-Belmonte, G., et al., "Charge Carrier Mobility and Lifetime of Organic Bulk Heterojunctions Analyzed by Impedance Spectroscopy," Organic Electronics 9(5):847-851, Oct. 2008.
Germack, D.S., et al., "Substrate-Dependent Interface Composition and Charge Transport in Films for Organic Photovoltaics," Applied Physics Letters 94(23):233303-1-233303-3, Jun. 2009.
Gilot, J., et al., "Double and Triple Junction Polymer Solar Cells Processed From Solution," Applied Physics Letters 90(14):143512-1-143512-3, Apr. 2007.
Goh, C., et al., "Effects of Molecular Interface Modification in Hybrid Organic-Inorganic Photovoltaic Cells," Journal of Applied Physics 101(11):114503-1-114503-12, Jun. 2007.

Grancini, G., et al., "Boosting Infrared Light Harvesting by Molecular Functionalization of Metal Oxide/Polymer Interfaces in Efficient Hybrid Solar Cells," Advanced Functional Materials 22(10):2160-2166, May 2012.
Gregg, B.A., et al., "On the Superlinear Increase in Conductivity With Dopant Concentration in Excitonic Semiconductors," Applied Physics Letters 84(10):1707-1709, Mar. 2004.
Gregg, B.A., and R.A. Cormier, "Doping Molecular Semiconductors: n-Type Doping of a Liquid Crystal Perylene Diimide," Journal of the American Chemical Society 123(32):7959-7960, Aug. 2001.
Guldi, D.M., et al., "Zwitterionic Acceptor Moieties: Small Reorganization Energy and Unique Stabilization of Charge Transfer Products," Journal of Physical Chemistry B 107(3):7293-7298, Jul. 2003.
Guldi, D.M., and M. Prato, "Excited-State Properties of $C_{60}$ Fullerene Derivatives," Accounts of Chemical Research 33(10):695-703, Oct. 2000.
Günes, S., et al., "Conjugated Polymer-Based Organic Solar Cells," Chemical Reviews 107(4):1324-1338, Apr. 2007.
Guo, S., et al., "n-Doping of Organic Electronic Materials Using Air-Stable Organometallics," Advanced Materials 24(5):699-703, Feb. 2012.
Haber, J., "Manual on Catalyst Characterization (Recommendations 1991)," Pure and Applied Chemistry 63(9):1227-1246, Jan. 1991.
Hau, S.K., et al., "Air-Stable Inverted Flexible Polymer Solar Cells Using Zinc Oxide Nanoparticles as an Electron Selective Layer," Applied Physics letters 92(25):253301-1-253301-3, Jun. 2008.
Hau, S.K., et al., "Effect of Chemical Modification of Fullerene-Based Self-Assembled Monolayers on the Performance of Inverted Polymer Solar Cells," ACS Applied Materials & Interfaces 2(7):1892-1902, Jul. 2010.
Hau, S.K., et al., "High Performance Ambient Processed Inverted Polymer Solar Cells Through Interfacial Modification With a Fullerene Self-Assembled Monolayer," Applied Physics Letters 93(23):233304-1-233304-3, Dec. 2008.
Hau, S.K., et al., "Interfacial Modification to Improve Inverted Polymer Solar Cells," Journal of Materials Chemistry 18(42):5113-5119, Nov. 2008.
Hau, S.K., et al., "Spraycoating of Silver Nanoparticle Electrodes for Inverted Polymer Solar Cells," Organic Electronics 10(4):719-723, Jul. 2009.
Hayakawa, A., et al., "High Performance Polythiophene/Fullerene Bulk-Heterojunction Solar Cell With a TiOx Hole Blocking Layer," Applied Physics Letters 90(16):163517-1-163517-3, Apr. 2007.
He, Y., et al., "Indene-C60 Bisadduct: A New Acceptor for High-Performance Polymer Solar Cells," Journal of the American Chemical Society 132(4):1377-1382, Feb. 2010.
He, Z., et al., "Largely Enhanced Efficiency With a PFN/Al Bilayer Cathode in High Efficiency Bulk Heterojunction Photovoltaic Cells With a Low Bandgap Polycarbazole Donor," Advanced Materials 23(27):3086-3089, Jul. 2011.
Horiuchi, T., et al., "High Efficiency of Dye-Sensitized Solar Cells Based on Metal-Free Indoline Dyes," Journal of the American Chemical Society 126(39):12218-12219, Oct. 2004.
Hsu, C.-W, et al., "Effect of Chemical Structure of Interface Modifier of $TiO_2$ on Photovoltaic Properties of Poly(3-hexylthiophene)/$TiO_2$ Layered Solar Cells," Journal of Colloid and Interface Science 321(1):182-187, Jan. 2009.
Huang, J.-S., et al., "Solution-Processed Vanadium Oxide as an Anode Interlayer for Inverted Polymer Solar Cells Hybridized With ZnO Nanorods," Organic Electronics 10(6):1060-1065, Sep. 2009.
Hummelen, J.C., et al., "Preparation and Characterization of Fulleroid and Methanofullerene Derivatives," Journal of Organic Chemistry 60(3):532-538, Feb. 1995.
Im, J.-H., et al., "6.5% Efficient Perovskite Quantum-Dot-Sensitized Solar Cell," Nanoscale 3(10):4088-4093, Oct. 2011.
Ishii, H., et al., "Energy Level Alignment and Interfacial Electronic Structures at Organic/Metal and Organic/Organic Interfaces," Advanced Materials 11(8):605-625, Jun. 1999.
Jung, J.W., et al., "Enhanced Performance and Air Stability of Polymer Solar Cells by Formation of a Self-Assembled Buffer Layer From Fullerene-End-Capped Poly(ethylene glycol)," Advanced Materials 23(15):1782-1787, Apr. 2011.

(56) References Cited

OTHER PUBLICATIONS

Kar, P., et al., "Interfacial Electron Transfer Dynamics Involving a New Bis-Thiocyanate Ruthenium(II)-Polypyridyl Complex, Coupled Strongly to Nanocrystalline $TiO_2$, Through a Pendant Catecholate Functionality," Journal of Physical Chemistry C 113(18):7970-7977, May 2009.

Kim, H.-S., et al., "Lead Iodide Perovskite Sensitized All-Solid-State Submicron Thin Film Mesoscopic Solar Cell With Efficiency Exceeding 9%," Scientific Reports 2:591, Nov. 2012, pp. 1-7.

Kim, J., et al., "New Architecture for High-Efficiency Polymer Photovoltaic Cells Using Solution-Based Titanium Oxide as an Optical Spacer," Advanced Materials 18(5):572-576, Mar. 2006.

Kim, J.Y., et al., "Efficient Tandem Polymer Solar Cells Fabricated by All-Solution Processing," Science 317(5835):222-225, Jul. 2007.

Kim, M.-S., et al., "Choice of Electrode Geometry for Accurate Measurement of Organic Photovoltaic Cell Performance," Applied Physics Letters 92(13):133301-1-133301-3, Mar. 2008.

Kojima, A., et al., "Organometal Halide Perovskites as Visible-Light Sensitizers for Photovoltaic Cells," Journal of the American Chemical Society 131(17):6050-6051, May 2009.

Krebs, F.C., "Air Stable Polymer Photovoltaics Based on a Process Free From Vacuum Steps and Fullerenes," Solar Energy Materials and Solar Cells 92(7):715-726, Jul. 2008.

Krebs, F.C., "Fabrication and Processing of Polymer Solar Cells: a Review of Printing and Coating Techniques," Solar Energy Materials and Solar Cells 93(4):394-412, Apr. 2009.

Krebs, F.C., "Polymer Solar Cell Modules Prepared Using Roll-to-Roll Methods: Knife-Over-Edge Coating, Slot-Die Coating and Screen Printing," Solar Energy Materials and Solar Cells 93(4):465-475, Apr. 2009.

Krebs, F.C., et al., "A Complete Process for Production of Flexible Large Area Polymer Solar Cells Entirely Using Screen Printing—First Public Demonstration," Solar Energy Materials and Solar Cells 93(4):422-441, Apr. 2009.

Krebs, F.C., et al., "A Simple Nanostructured Polymer/ZnO Hybrid Solar Cell—Preparation and Operation in Air," Nanotechnology 19(42):424013, Oct. 2008, pp. 1-13.

Kuang, D., et al., "A New Ion-Coordinating Ruthenium Sensitizer for Mesoscopic Dye-Sensitized Solar Cells," Inorganica Chemica Acta 361(3):699-706, 2008.

Kuang, D. et al.' "Ion Coordinating Sensitizer for High Efficiency Mesoscopic Dye-Sensitized Solar Cells: Influence of Lithium Ions on the Photovoltaic Performance of Liquid and Solid-State Cells," Nano Letters 6(4):769-773, Apr. 2006.

Kumar, A., et al., "High Efficiency Polymer Solar Cells With Vertically Modulated Nanoscale Morphology," Nanotechnology 20(16):165202, Apr. 2009, 4 pages.

Lee, C.T.Y., et al., "Development of the Colle-Salvetti Correlation-Energy Formula Into a Functional of the Electron Density," Physical Review B 37(2):785-789, Jan. 1988.

Lee, H.J., et al., "Panchromatic Response Composed of Hybrid Visible-Light Absorbing Polymers and Near-IR Absorbing Dyes for Nanocrystalline $Tio_2$-Based Solid-State Solar Cells," Journal of Power Sources 196(1):596-599, Jan. 2011.

Lee, K., et al., "Air-Stable Polymer Electronic Devices," Advanced Materials 19(18):2445-2449, Sep. 2007.

Lee, M.M., et al., "Efficient Hybrid Solar Cells Based on Meso-Superstructured Organometal Halide Perovskites," Science 338(6107):643-647, Nov. 2012.

Lee, S.T., et al., "Metal Diffusion From Electrodes in Organic Light-Emitting Diodes," Applied Physics Letters 75(10):1404-1406, Sep. 1999.

Leijtens, T., et al., "Charge Density Dependent Mobility of Organic Hole-Transporters and Mesoporous $TiO_2$ Determined by Transient Mobility Spectroscopy: Implications to Dye-Sensitized and Organic Solar Cells," Advanced Materials 25(23):3227-3233, Jun. 2013.

Lenes, M., et al., "Fullerene Bisadducts for Enhanced Open-Circuit Voltages and Efficiencies in Polymer Solar Cells," Advanced Materials 20(11):2116-2119, Jun. 2008.

Li, C.-Z., et al., "Effective Interfacial Layer to Enhance Efficiency of Polymer Solar Cells Via Solution-Processed Fullerene-Surfactants," Journal of Materials Chemistry 22(17):8574-8578, May 2012.

Li, C.-Z., et al., "Evaluation of Structure—Property Relationships of Solution-Processible Fullerene Acceptors and Their N-Channel Field-Effect Transistor Performance," Journal of Materials Chemistry 22(30):14976-14981, Aug. 2012.

Li, C.-Z., et al., "Functional Fullerenes for Organic Photovoltaics," Journal of Materials Chemistry 22(10):4161-4177, Mar. 2012.

Li, C.-Z., et al., "Solution-Processable Highly Conducting Fullerenes," Advanced Materials 25(17):2457-2461, May 2013.

\* cited by examiner

C₆₀-bis

FULLERENE SURFACTANTS AND THEIR USE IN POLYMER SOLAR CELLS

CROSS-REFERENCE TO RELATED APPLICATION

This application claims the benefit of U.S. Patent Application No. 61/566,943, filed Dec. 5, 2011, expressly incorporated herein by reference in its entirety.

STATEMENT OF GOVERNMENT LICENSE RIGHTS

This invention was made with Government support under FA2386-11-1-4072 awarded by the Air Force Office of Scientific Research, N00014-11-1-0300 awarded by the Office of Naval Research, and DE-FC3608GO18024/A000 awarded by the Department of Energy. The Government has certain rights in the invention.

BACKGROUND OF THE INVENTION

Effective control of organic-metal interfaces is critical for achieving high-performance polymer solar cells (PSCs). Ideally, the work-function ($\Phi$) of the cathode and anode should be aligned with the energy of the photo-excited quasi-Fermi levels ($E_F$) of organic semiconductors to create Ohmic contact for maxing achievable open-circuit voltage ($V_{oc}$) and minimized energy barrier for charge-extraction. Although low $\Phi$ metal such as Ca ($\Phi$=2.9 eV) has been proved to form good contact with bulk heterojunction (BHJ) layer as cathode, its vulnerability to environmental conditions undermines its use for practical applications. More stable metals like Al ($\Phi$=4.28 eV) and Ag ($\Phi$=4.57 eV) have been used as cathode, but their relatively high $\Phi$ often cause energy mismatch between BHJ blends and themselves, which results in lower $V_{oc}$ and device performance.

To alleviate this problem, proper interfacial engineering by inserting a thin layer between cathode and active layer has been vigorously explored. For example, inorganic materials such as LiF and $Cs_2CO_3$ and metal oxides ($TiO_x$, $ZnO_x$), and organic materials such as insulating poly(ethylene oxide) (PEO) and conjugated polyelectrolyte (CPE) have also been proved to be effective in improving Al cathode based device performance. In a recent study, 8.37% of PCE was reported by inserting polyfluorene derivative (PFN) between the high performance PTB7:PC71BM BHJ and Ca/Al. In addition, self-assembled fullerenes (e.g., PCBM capped PEG and fluorocarbon modified PCBM (F-PCBM)) have also been reported to increase P3HT:PCBM based device performance.

Despite that interface engineering has been performed for conventional PSCs, the performances obtained from Ag-based devices were usually lower than those using Ca/Al and Al cathode. This significantly limits the utilization of stable and reflective Ag as cathode for improving performance and stability of devices, though it is well-known Ag anode can be advantageous in inverted PSCs to facilitate the printing process.

On the other hand, fullerene-based materials not only can match well with the energy level of the lowest unoccupied molecular orbital (LUMO) of commonly used acceptor (e.g., PCBM), but also possess sufficiently deep highest occupied molecular orbital (HOMO) energy level, which make them as energetically ideal candidates for electron transport layer (ETL) to facilitate electron-selecting and hole-blocking in PSCs.

Despite the advances in the development of materials to enhance solar cell performance, a need exists to provide effective interfacial materials that are capable of adjusting the $\Phi$ of cathode to improve the contact with the BHJ layer, possess reasonable electron mobility to minimize electrical resistance across the interfacial layer, and have sufficient orthogonal solvent-processibility and film forming properties to avoid eroding into the BHJ layer. The present invention seeks to fulfill this need and provides further related advantages.

SUMMARY OF THE INVENTION

The present invention provides fullerene surfactant compounds that can be incorporated into polymer solar cells as an interfacial layer intermediate the cells' active layer and cathode to enhance solar cell efficiency.

In one aspect the invention provides a fullerene compound, comprising:
(a) a fullerene group;
(b) one or more cationic nitrogen centers covalently coupled to the fullerene group;
(c) one or more hydrophilic groups covalently coupled to the fullerene group; and
(d) one or more counter ions associated with the cationic nitrogen center.

Representative fullerene groups include $C_{60}$, $C_{70}$, $C_{76}$, $C_{78}$, $C_{82}$, $C_{84}$, and $C_{92}$ fullerene groups. In one embodiment, the fullerene group is a $C_{60}$ fullerene group. In one embodiment, the cationic nitrogen center is a quaternary amine group. Suitable hydrophilic groups include polyether and polyol groups. In certain embodiments, the polyether group is a polyalkene oxide group such as a polyethylene oxide group having the formula —$(CH_2CH_2O)_n$—, where n is from 1 to about 20. In certain embodiments, the fullerene compound further includes comprising an anionic center. Representative anionic centers include sulfonate ($SO_3^{2-}$) and carboxylate (—$CO_2^-$) groups. In one embodiments, the fullerene compound is a mono-fulleropyrrolidium. In other embodiment, the fullerene compound is a bis-fulleropyrrolidium.

In one embodiment, the compound has the structure:

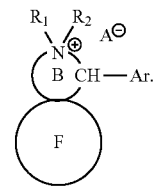

In another embodiment, the compound has the structure:

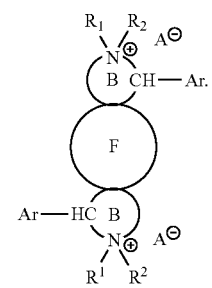

In these embodiments, F is a fullerene group; B is a N-containing ring having from 5-7 ring atoms; $R_1$ and $R_2$ are independently selected from the group consisting of a polyalkylene oxide and a C1-C20 alkyl optionally substituted with an anionic center; Ar is —$C_6H_5$-PEO, wherein —$C_6H_5$-PEO is selected from the group consisting of mono-, di-, tri-, and tetra-PEO substituted phenyl; and $A^-$ is a counter ion associated with the cationic nitrogen center.

In another aspect of the invention, photovoltaic devices are provided. In certain embodiments, the photovoltaic device includes an interfacial layer intermediate the cathode and active layer, wherein the interfacial layer includes one or more fullerene surfactant compounds of the invention. In one embodiment, the photovoltaic device includes:

(a) a first electrode;

(b) an active layer disposed on a surface of the first electrode;

(c) a layer comprising a fullerene compound of the invention disposed on a surface of the active layer opposite the first electrode; and (d) a second electrode disposed on a surface of the layer comprising the fullerene compound of the invention opposite the active layer.

In another embodiment, the device further includes a hole transport layer intermediate the first electrode and the active layer.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

The present invention provides fullerene surfactants and their use to modify the interface of the cathode and bulk heterojunction layer in organic solar cells. The incorporation of an interfacial layer including a fullerene surfactant of the invention in a conventional polymer solar cell enhances the efficiency of the solar cell.

In one aspect, the invention provides a fullerene surfactant. As used herein, the term "fullerene surfactant" refers to a fullerene that includes hydrophilic group sufficient to render the fullerene solution processible in the fabrication of polymer solar cells. The fullerene surfactant includes a fullerene group, one or more cationic amine centers, one or more hydrophilic groups, and one or more counter ions. The cationic amine group is covalently coupled to the fullerene group. The hydrophilic group is covalently the fullerene group. In certain embodiments, the hydrophilic group is covalently coupled to the fullerene group through the cationic amine group. In certain embodiments, the fullerene surfactant further includes an anionic center.

Representative fullerene groups include $C_{60}$, $C_{70}$, $C_{76}$, $C_{78}$, $C_{82}$, $C_{84}$, and $C_{92}$ fullerene groups. In one embodiment, the fullerene surfactant of the invention includes a $C_{60}$ group.

The cationic amine group is a positively-charged amine center. Suitable cationic amine groups include quaternary amine groups prepared by quaternizing amine precursor compounds. In certain embodiments, the fullerene surfactants of the invention are prepared by quaternization of precursor fullerene amine compounds.

Representative hydrophilic groups include one or more hydrophilic substituents such as ether and alcohol groups. In certain embodiments, the hydrophilic group is a polyether group. Representative polyether groups include polyalkylene oxides with as polyethylene oxide (PEO) groups, polypropylene oxide (PPO) groups, and groups that include ethylene oxide and propylene oxide groups. Suitable polyethylene oxide groups have the formula $-(CH_2CH_2O)_n-$, where n is from 1 to about 20, and $-(CH(CH_3)CH_2O)_n-$, where n is from 1 to about 20. In other embodiments, the hydrophilic group is a polyol.

In embodiments of the fullerene surfactants that include anionic centers, representative anionic centers include sulfonate ($SO_3^{2-}$) and carboxylate ($-CO_2^-$) groups. The anionic centers are covalently coupled to the fullerene group.

Figure 1:
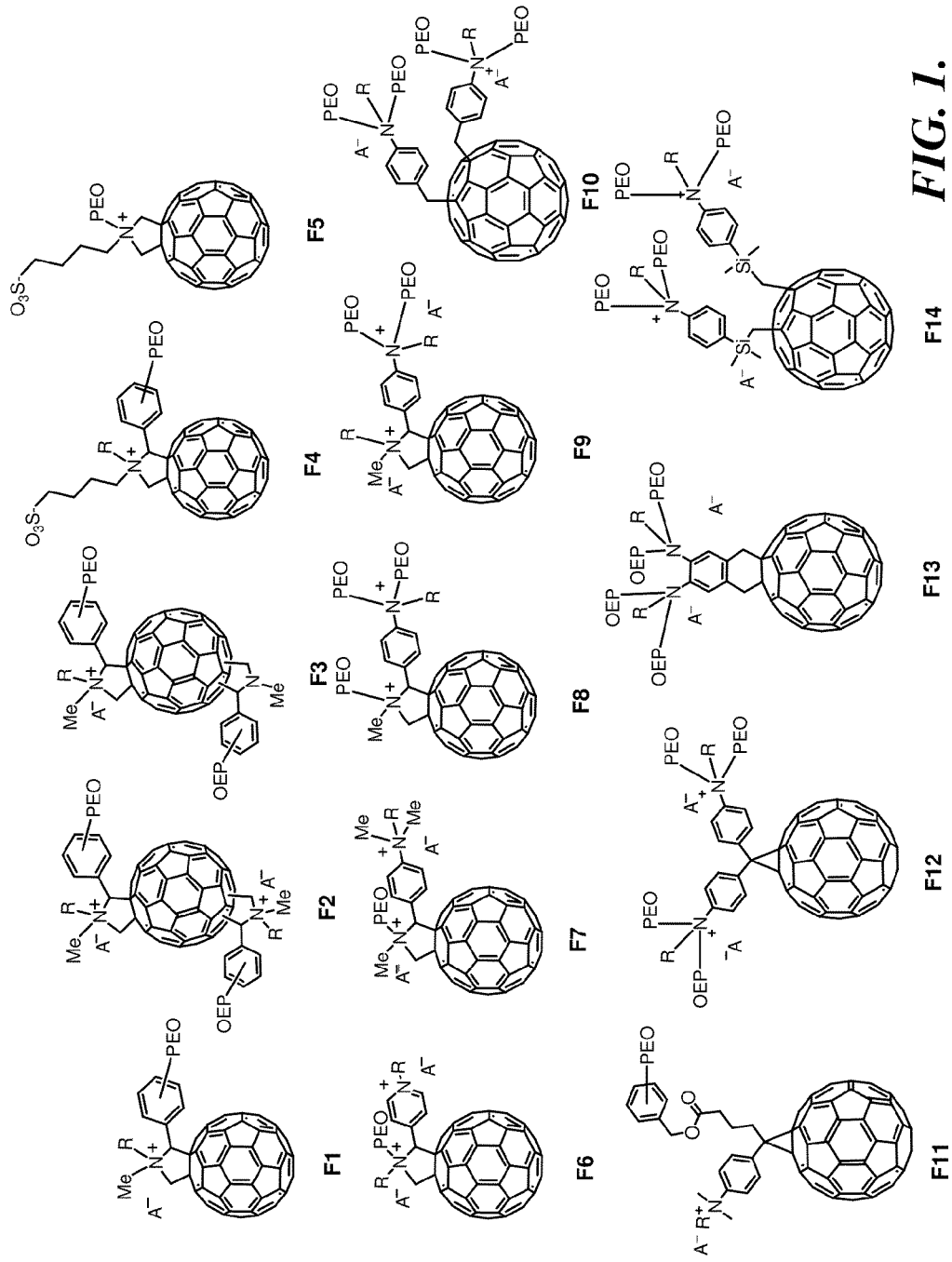
FIG. 1 illustrates the structures of representative fullerene surfactants of the invention.

Representative fullerene surfactants of the invention are illustrated in FIG. 1. Referring to fullerene surfactant compounds F1-F14 in FIG. 1, the fullerene group may be any one of $C_{60}$, $C_{70}$, $C_{76}$, $C_{78}$, $C_{82}$, $C_{84}$, and $C_{92}$ fullerene groups; R is independently selected from the group consisting of C1-C20 straight chain and branched alkyl; PEO is an alkylene oxide group independently selected from the group consisting of polyethylene oxide having the formula $-(CH_2CH_2O)_n-$, where n is from 1 to about 20 or polypropylene oxide having the formula $-(CH(CH_3)CH_2O)_n-$, where n is from 1 to about 20; $-C_6H_5$-PEO is selected from the group consisting of mono-, di-, tri-, and tetra-PEO substituted phenyl; and $A^-$ is a counter ion selected from the group consisting of fluoride, chloride, bromide, iodide, trifluoromethyl sulfonyl ($CF_3SO_3^-$), tetrakis(imidazolyl)borate ($BIm_4^-$), and tetrakis (3,5-bis(trifluoromethyl)phenyl]borate ($TFPB^-$).

In one embodiment, the fullerene surfactant compounds of the invention have formula (IA):

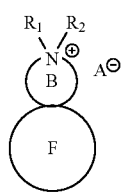

(IA)

In another embodiment, the fullerene surfactant compounds of the invention have formula (IB):

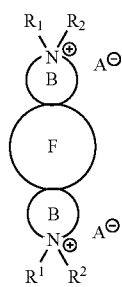

(IB)

In a further embodiment, the fullerene surfactant compounds of the invention have formula (IIA):

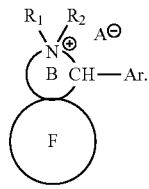

(IIA)

In another embodiment, the fullerene surfactant compounds of the invention have formula (IIB):

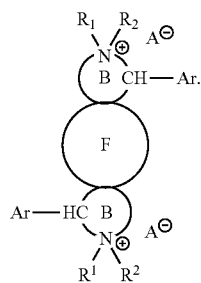

(IIB)

In one embodiment, the fullerene surfactant compounds of the invention have formula (III):

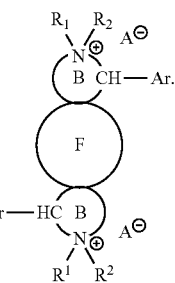

(III)

In another embodiment, the fullerene surfactant compounds of the invention have formula (IV):

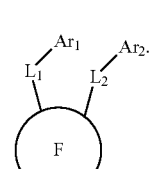

(IV)

In one embodiment, the fullerene surfactant compounds of the invention have formula (V):

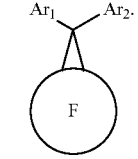

(V)

In another embodiment, the fullerene surfactant compounds of the invention have formula (VI):

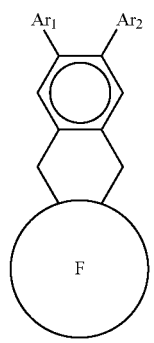

(VI)

For fullerene surfactant compounds noted above (i.e., compounds of formula (IA)-(VI)), F is a fullerene group (e.g., $C_{60}$, $C_{70}$, $C_{76}$, $C_{78}$, $C_{82}$, $C_{84}$, and $C_{92}$); B is a N-containing ring fused to the fullerene group and having from 5-7 ring atoms (e.g., pyrrolidine, a 5-membered ring); $R_1$ and $R_2$ are independently selected from the group consisting of a poly-alkylene oxide (e.g., PEO or PPO), as described above, and a C1-C20 alkyl optionally substituted with an anionic center (e.g., sulfonyl or carboxyl); Ar, $Ar_1$, and $Ar_2$ are independently selected from the group consisting of —$C_6H_5$-PEO, —$C_6H_5$—$N^+(PEO)_2R_1|A^-$; and —$C_5H_4N^+$—$R_1|A^-$, wherein —$C_6H_5$-PEO is selected from the group consisting of mono-, di-, tri-, and tetra-PEO substituted phenyl, wherein —$C_6H_5$—$N^+(PEO)_2R_1$ is a substituted aniline, and wherein —$C_5H_4N^+$—$R_1$ is a substituted pyridinium; $L_1$ and $L_2$ are linkers having from 1 to 20 carbon atoms (e.g., C1-C20 alkylene) optionally including one or more heteroatoms (e.g., O, N, or S) and/or one or more functionalized carbon atoms (e.g., C=O); and $A^-$ is a counter ion associated with the cationic nitrogen center.

Figure 2:
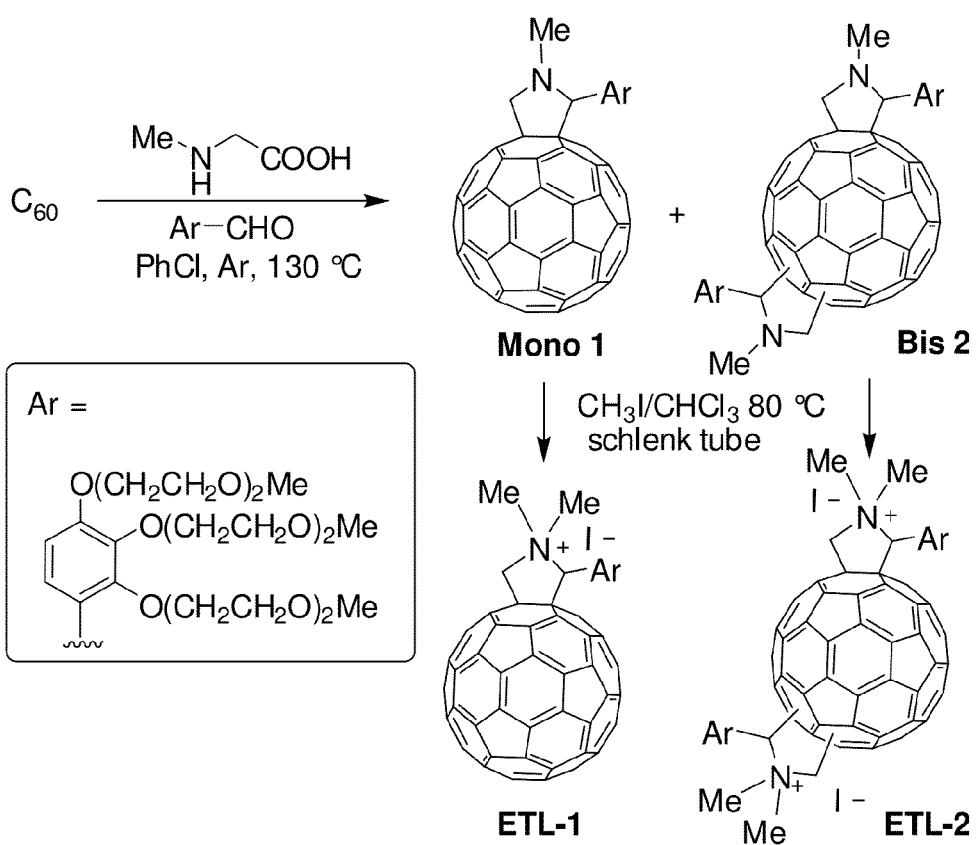
FIG. 2 is a schematic illustration of the preparation of two representative fullerene surfactants of the invention, ETL-1 and ETL-2.

The preparation of two representative fullerene surfactants of the invention, ETL-1 and ETL-2, is illustrated schematically in FIG. 2 and described in Example 1.

By virtue of its component groups, the fullerene surfactant of the invention is advantageously soluble in a solvent orthogonal to the device active layer. In practice of the method of the invention, device fabrication includes forming a layer intermediate the active layer and cathode. Application of the fullerene surfactant to the active layer provides a fullerene surfactant layer onto which the cathode is formed.

Figure 3:
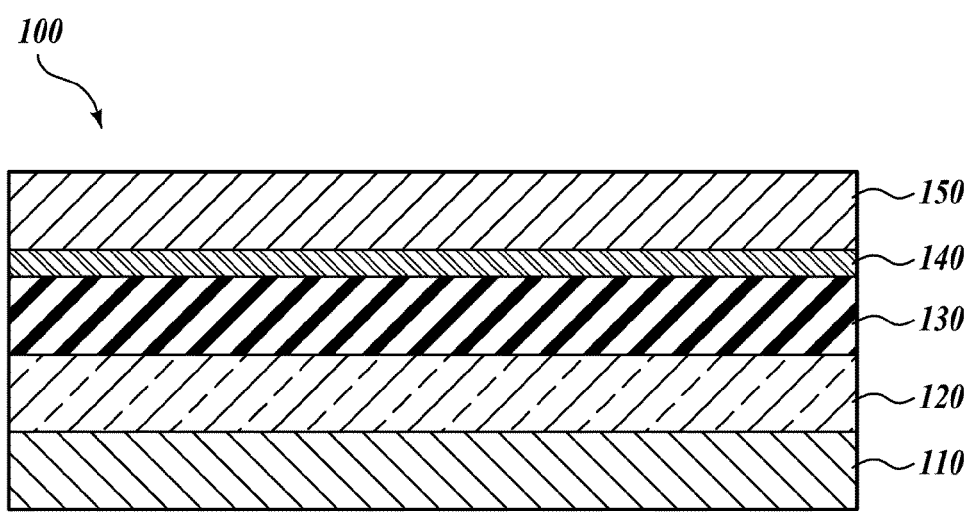
FIG. 3 is a cross-sectional view of a representative photovoltaic device of the invention incorporating a fullerene surfactant-containing interfacial layer intermediate the cathode and the active layer.

FIG. 3 is a cross-sectional view of a typical heterojunction photovoltaic device in accordance with one embodiment of the invention. Referring to FIG. 3, photovoltaic device 100 includes first electrode 110 (anode), hole transport layer 120 (also referred to as a charge transport or charge selective layer) formed on first electrode 110, photovoltaic layer 130 (also referred to as the active layer) formed on charge transport layer 120, fullerene surfactant-containing layer 140 (also referred to as electron transport or electron selective layer and also referred to herein as the "interfacial layer") formed on photovoltaic layer 130, and second electrode 150 (cathode) formed on fullerene surfactant-containing layer 140. Photovoltaic layer 130 is the active layer, such as a BHJ layer.

In the devices of the invention, the hole transport and electron transport layers define the charge collection properties in the devices. The best devices reported to date are composed of a layer of polymer donor and fullerene acceptor bulk-heterojunction (BHJ) film sandwiched between a transparent electrode, such as indium tin oxide (ITO), and a metal electrode. Under illumination, photo-generated excitons will dissociate at the donor-acceptor interface, driven by the difference in energy levels between the two semiconductors. The separated charges will then drift under the inherent electric field created by the work-function difference between the asymmetric electrodes and ultimately, will be collected by the corresponding electrodes. The PCE is defined by the product of three parameters including short-circuit current density ($J_{sc}$), open-circuit voltage ($V_{oc}$), and fill factor (FF).

The nature of electrical contact between the active BHJ layer and the electrodes can significantly affect all three device-related parameters and modification of those interfaces by inserting appropriate interfacial layers can significantly alter the contact properties to improve the PCE of OPVs. The interfacial layer of the invention serves multiple functions that include:

(a) tuning the energy level alignment at the electrode/active layer interface;

(b) defining polarity of electrodes and improving charge selectivity;

(c) controlling surface properties to alter the morphology of the active layer;

(d) introducing optical spacer and plasmonic effects to modulate light absorption in the active layer; and (e) improving interfacial stability between the active layer and electrodes.

The photovoltaic layer (or active layer) can include any one of a variety of materials and mixtures of materials as known in the art. Representative useful materials include P3HT, PIDT-PhanQ, PECz-DTQx, PCDTBT, PDTSTPD, PDTGTPD, PTB7. Representative active fullerene materials include PCBM and ICBA. Other representative active fullerene materials suitable for inclusion in a photoactive layer include those described in U.S. Patent Application Publication No. US 2011/0132439, incorporated herein by reference in its entirety.

The following is a description of representative fullerene surfactants of the invention and their use in interfacial layers to enhance the efficiency of polymer solar cells.

Figure 4A:
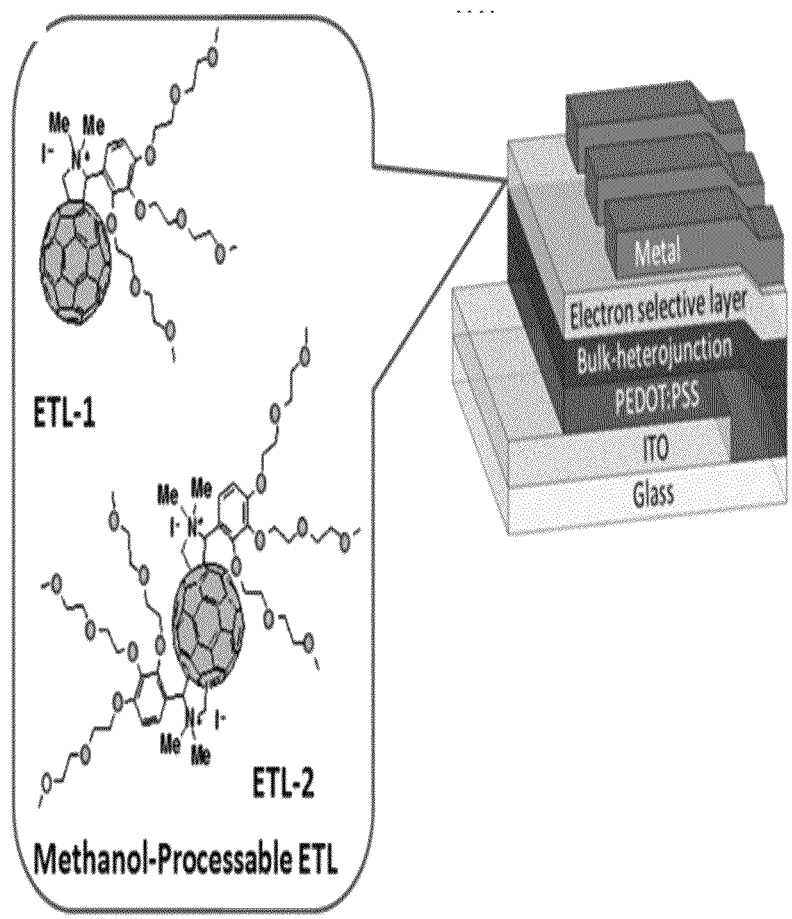
FIG. 4A is a schematic illustration of the use of two representative fullerene surfactants of the invention, ETL-1 and ETL-2, as interfacial layers in a PIDT-PhanQ:$PC_{71}BM$ polymer solar cell device.
Figure 4B:
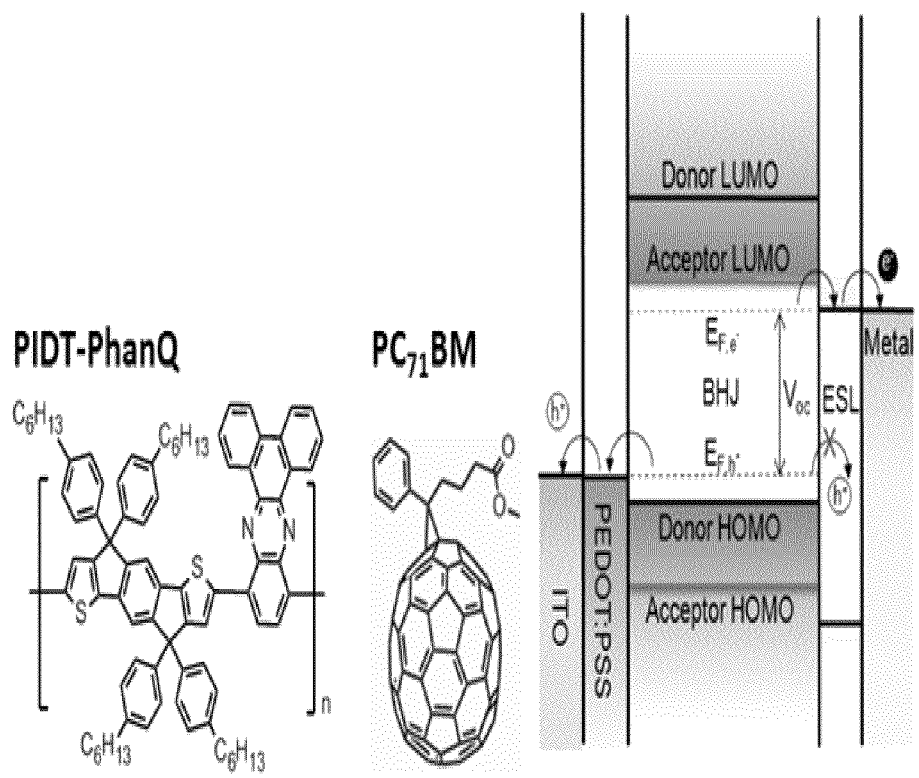
FIG. 4B is a schematic energy diagram of the device shown in FIG. 4A: PIDT-PhanQ:poly(indacenodithiophene-co-phananthrene-quinoxaline) $PC_{71}BM$: [6,6]-phenyl C71-butyric acid methyl ester.

The present invention provides fullerene surfactants, ETL-1 and ETL-2, that can be readily dissolved in alcoholic solvents and applied as interfacial layer for cathode (see FIG. 4A), which exhibited effective tuning of cathode Φ, extraction of electrons, and photocurrent generation in devices. These two fullerene surfactants intrinsically help forming interfacial contact between metal (in either high or low Φ) and BHJ to improve device performance. Recently, the mechanism of using fullerene surfactant to enhance device $V_{oc}$ has been elucidated that the metal $E_F$ is pinned to the LUMO energy level of interfacial layer, thus increasing the device's $V_{oc}$ regardless of the choice of different cathode metal. The present invention provides an organic interfacial material to realize Ag cathode based OPV with superior performance (as high as 6.63%) to those of Ca/Al and Al based devices due to the solvent-processed fullerene ETL simultaneously enhanced $V_{oc}$, $J_{oc}$, and FF of device.

ETL-1 and ETL-2 having compact integration of both ionic moieties and polar ethylene oxide chains onto a $C_{60}$ core were prepared by quaternizing the tertiary nitrogen of fulleropyrrolidines with methyl iodide (FIG. 2). Comparing to the poor solubility of most fullerene derivatives (e.g., Mono 1, Bis 2 and PCBM) in polar solvents, fulleropyrrolidiniums (ETL-1 and ETL-2) exhibit amphiphilic properties that can be dissolved in both chloroform and methanol, which provides great flexibility for processing in orthogonal-solvents to prevent eroding bottom BHJ layer.

The energy levels of ETL-1 and ETL-2 were estimated by cyclic voltammogram measurements. As shown in Table 1, the LUMOs of ETLs exhibit small energy-gradient compared to that of PCBM due to that the electron-deficient cationic nitrogen is in close vicinity of the fullerene core, which made this interfacial material energetically favor electron collection and transport from PCBM to cathode.

TABLE 1

Reduction Potentials and estimated LUMO for fullerene surfactants.[a]

|  | $E_{1/2}^{red}$ vs. Fc/Fc$^+$ | | | LUMO[b] | LUMO[c] |
|---|---|---|---|---|---|
|  | $E_1$ (V) | $E_2$ (V) | $E_3$ (V) | (eV) | (eV) |
| ETL-1 | 0.87 | 1.39 | 2.05 | 3.93 | 4.44 |
| ETL-2 | 0.90 | 1.43 | — | 3.90 | 4.39 |
| PC$_{71}$BM | 0.99 | 1.53 | 2.04 | 3.81 | 4.30 |

[a]Potential in volt vs. a ferrocene/ferrocenium couple.
[b]The LUMO levels were estimated using the following equation: LUMO level = −(4.8 + $E_{1/2}^{red1}$) eV.
[c]correlated LUMOs according to PCBM standard (LUMO = −4.30 eV).

Both ETL surfactants possess reasonable electron motilities (2.18×10$^{-4}$ cm$^2$ V$^{-1}$ s$^{-1}$ for ETL-1 and 4.91×10$^{-6}$ cm$^2$ V$^{-1}$ s$^{-1}$ for ETL-2), and show negligible absorbance to visible light, which qualify them as proper electron-transporting layer (ca. 10 nm). ETL-1 and ETL-2 bearing cationic nitrogen and PEO linkage effectively up-shifted the $\Phi$ of Al and Ag, around 0.8 eV by X-ray photoelectron spectroscopy (XPS) studies. It may be due to the polar interaction between fullerene surfactants and metal facilitate pinning of the metal $E_F$ to that of the ETLs upon equilibration, which reduced energy barrier between BHJ layer and cathodes. This, in turn, increases $V_{oc}$ and charge extraction efficiency.

The presence of these fullerene layers creates only minimal energy barrier height for electron extraction from PCBM (due to matched ETL LUMOs to that of PCBM). This is different from using the insulating PEO and p-type CPE process that have unfavored energy level and charge-transporting properties. Moreover, the n-type nature of fullerene surfactant layer creates an extra acceptor-donor junction that can potentially enhance exciton dissociation and prevent cathode from forming direct contact with active layer to quench excitons. These rationale are supported, vide infra, by the enhanced performance of PSCs with spun interfacial layers.

Figure 5A:
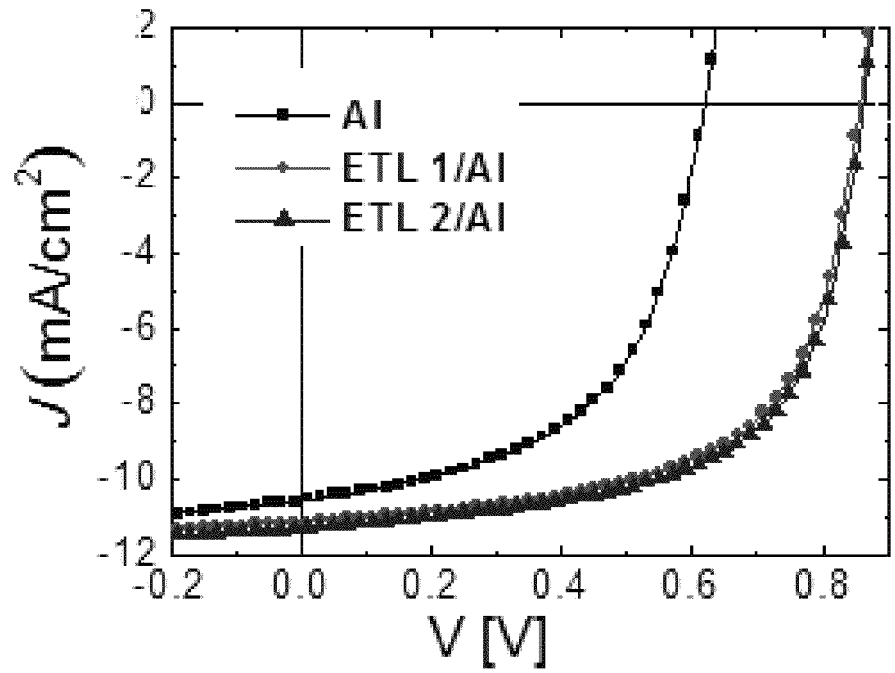
FIGS. 5A-5F compare the current density-voltage (J-V) characteristics of devices under illumination of AM 1.5 G at 100 mW $cm^{-2}$ for Al, Ca/Al, and Ag cathodes (FIGS. 5A, 5C, and 5E), respectively, and their corresponding external quantum efficiency (EQE) spectra (FIGS. 5B, 5D, and 5F).
Figure 5B:
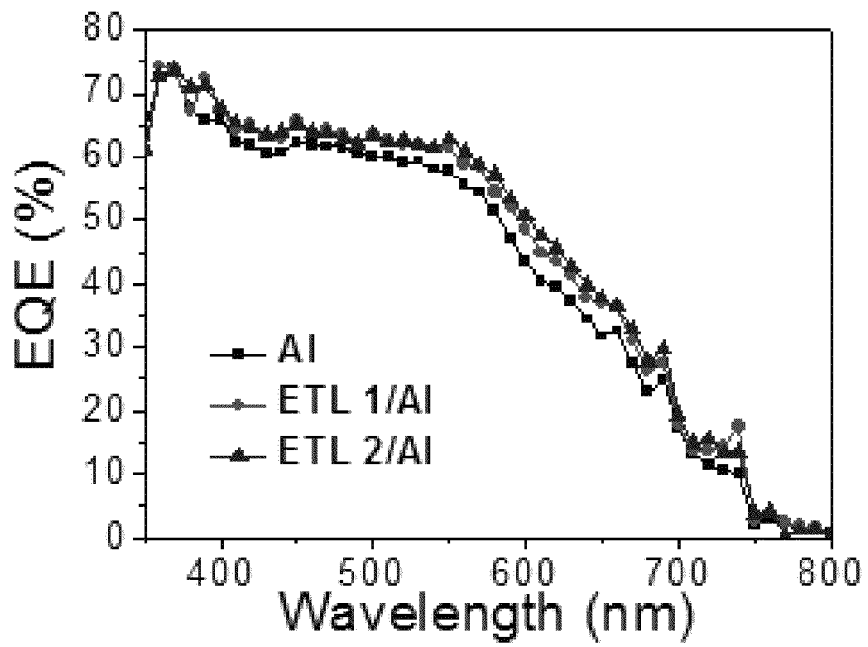

PSCs with fullerene surfactant-modified Al were studied. Device configuration of ITO/PEDOT:PSS/PIDT-PhanQ:PC$_{71}$BM/ETL/Al (FIG. 4A) showed significantly improved $V_{oc}$, and FF compared to those from the reference device without the interfacial layer (FIGS. 5A, 5B, and Table 2). The reference device A with bare Al as cathode showed a relatively low PCE of 3.54% with a $V_{oc}$ of 0.61 V, a $J_{sc}$ of 10.55 mA cm$^{-2}$, and a FF of 0.55. The Schottky-barrier at the active layer/Al interface caused low $V_{oc}$, $L_{sc}$, and FF. However, when a thin layer (about 10 nm) of ETL-1 or ETL-2 was inserted between the BHJ layer and Al, higher PCE of 5.96% (device B) and 6.03% (device C) could be achieved, which accounts for a 70% improvement for device C compared to the reference device. All the parameters ($J_{sc}$, $V_{oc}$ and FF) increased significantly for devices B and C, because a better interfacial contact was created between BHJ and Al when the fullerene ETL was applied, which lowered the $\Phi$ of Al, thus giving higher $V_{oc}$, and efficient electron extraction to give higher $J_{sc}$ and FF.

TABLE 2

Characteristics of Devices A-F.

| Device | Cathode | $V_{oc}$ [V] | $J_{sc}$ [mA/cm$^2$] | FF | PCE [%] |
|---|---|---|---|---|---|
| A | Al | 0.61 | 10.55 (10.34) | 0.55 | 3.54 |
| B | ETL-1/Al | 0.86 | 11.17 (11.09) | 0.62 | 5.96 |
| C | ETL-2/Al | 0.86 | 11.31 (11.27) | 0.62 | 6.03 |
| D | Ca/Al | 0.86 | 11.08 (10.64) | 0.63 | 6.00 |
| E | ETL-1/Ca/Al | 0.87 | 11.12 (11.07) | 0.64 | 6.19 |
| F | ETL-2/Ca/Al | 0.88 | 11.36 (11.20) | 0.65 | 6.50 |
| G | Ag | 0.74 | 10.92 (10.96) | 0.57 | 4.61 |
| H | ETL-1/Ag | 0.87 | 11.28 (11.11) | 0.64 | 6.28 |
| I | ETL-2/Ag | 0.88 | 11.41 (11.30) | 0.66 | 6.63 |

The values in parentheses were calculated from EQE spectrum.

Figure 5C:
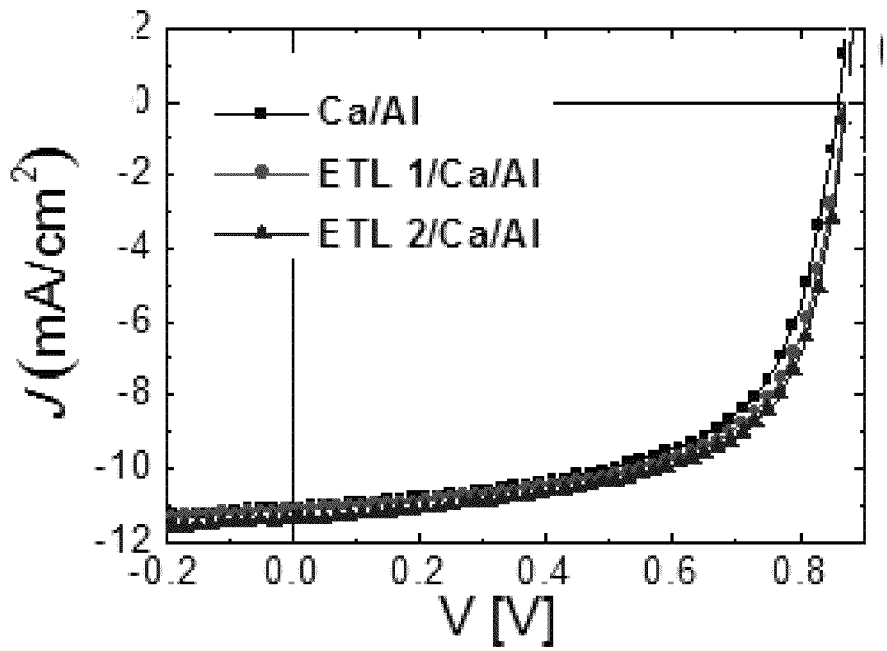
Figure 5D:
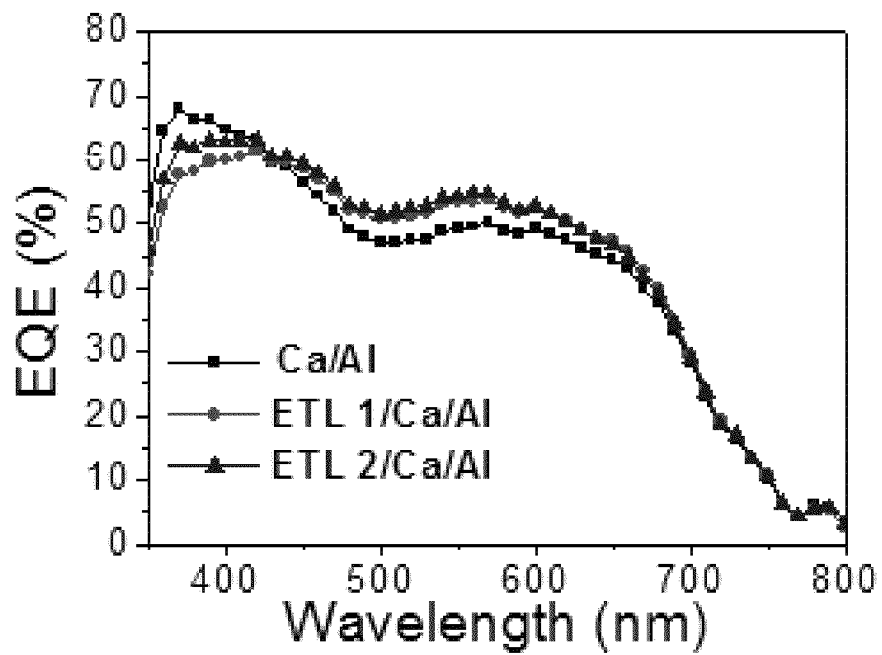
Figure 5E:
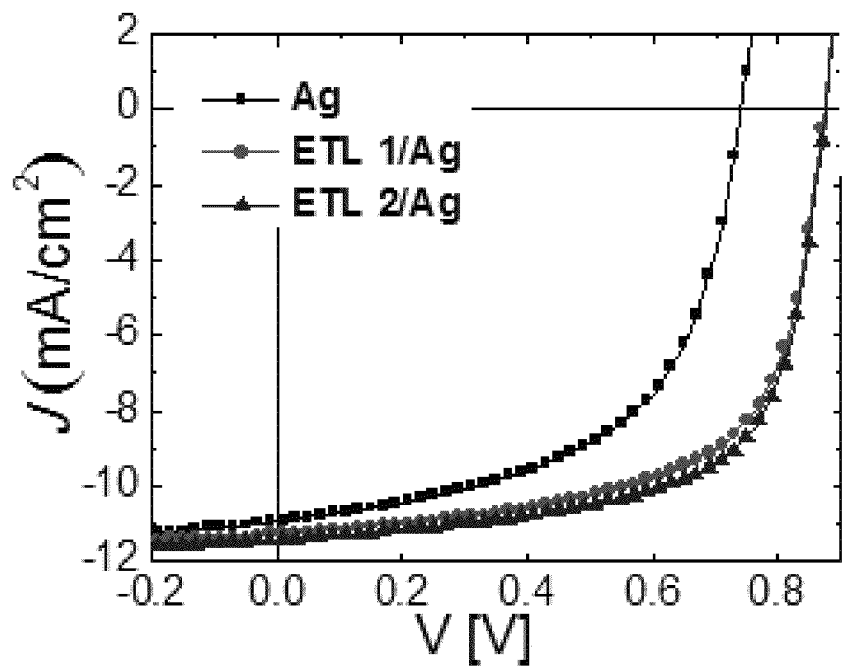
Figure 5F:
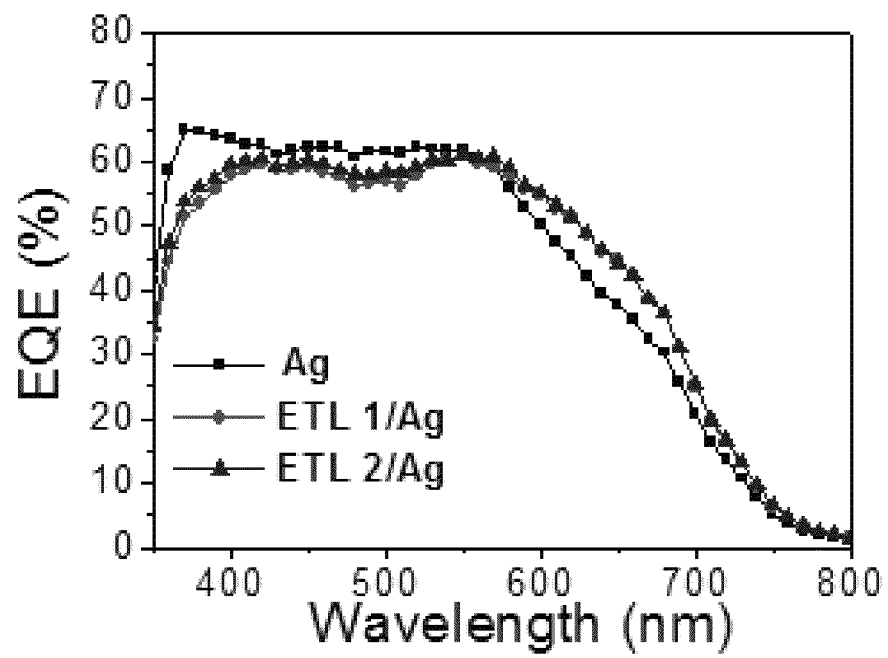

To further understand the effect on surfactant-modified cathodes, the commonly adopted Ca/Al cathode based device were also studied, in the device configuration of ITO/PEDOT:PSS/PIDT-PhanQ:PC$_{71}$BM/ETL/Ca/Al. Good contact between Ca/Al cathode and BHJ can give essentially high-performance, 6% PCE of device D ($V_{oc}$=0.86 V, $J_{sc}$=11.08 mA cm$^{-2}$, and FF=0.63). Slight improvements of device characteristics could be observed when the ETL layer was applied (FIGS. 5C, 5D, and Table 2). Improved PCE of 6.19% (ETL-1, device E) and 6.50% (ETL-2, device F) were achieved, which correlated to the slightly enhanced $V_{oc}$, $J_{sc}$ and FF. These results indicated that the additional fullerene ETL layer helped optimize the contact between Ca/Al and BHJ layer leading to increased PCE. Although being widely used in PSCs as electrodes, Al and Ca/Al are sensitive to air and moisture, which cause device degradation in ambient. Ag shows relatively good stability toward ambient condition. However, the energy mismatch between high $\Phi$ of Ag and LUMO of PCBM usually resulted in poor device performance. To alleviate this problem, devices were fabricated with the configuration of ITO/PEDOT:PSS/PIDT-PhanQ:PC$_{71}$BM/ETL/Ag (devices G-I). A distinctly improved PCE (44%) could be achieved for device I compared to that of reference device G due to enhanced $V_{oc}$, $J_{sc}$ and FF (FIGS. 5E, 5F, and Table 2). PCE of 6.63% from device I using ETL-2 is one of the highest values achieved from conventional PSC with Ag cathode.

The external quantum efficiency (EQE) spectra of devices A-I (FIGS. 5B, 5D, and 5F) were compared. The calculated $J_{sc}$ obtained from integration of EQE spectrum match well with measured one, with variation of less than 5% (Table 2). With an ETL-1 or ETL-2, the EQE of devices are higher in part of the spectrum compared to those of reference device, which correlate well with the results of higher photocurrents.

Figure 6:
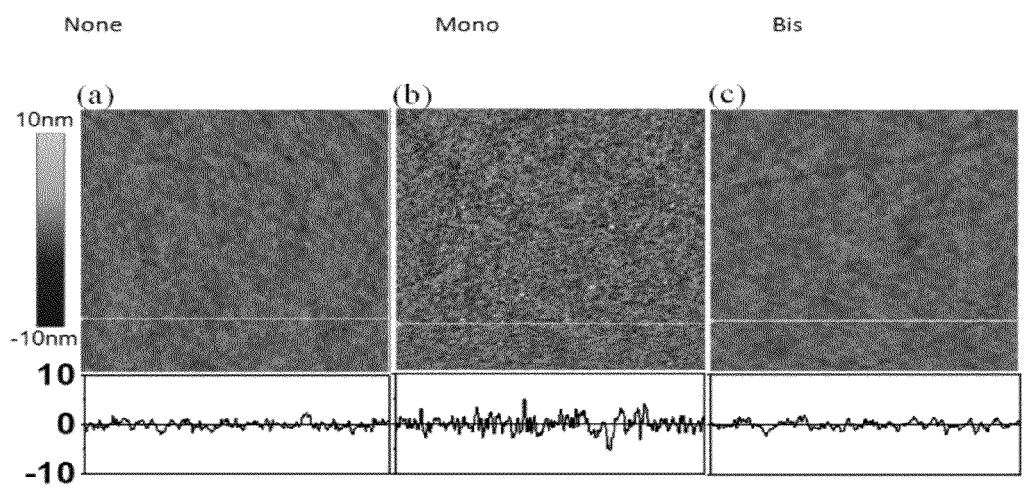
FIG. 6 compares surface morphology (5 μm×5 μm) and surface profile (10 nm to −10 nm) of PIDT-PhanQ:$PC_{71}BM$ BHJ based device: (a) BHJ only, (b) ETL-1 on BHJ, (c) ETL-2 on BHJ. RMS roughness for (a) 0.733 nm, (b) 1.01 nm, (c) 0.763 nm, respectively.

In all devices, ETL-1 show slightly lower PCE and relevant parameters ($J_{sc}$ and FF) than those of ETL-2, which may be due to the difference of film quality of these two ETLs on top of the BHJ layer. The topography and surface profile of devices with and without ETL layer were characterized by atomic force microscopy (AFM) and is shown in FIG. 6. All the interfacial layers covered well on top of BHJ layer. The surface of ETL-2 is relatively smooth as indicated by the lower root-mean-square (RMS) roughness, 0.763 nm (FIG. 6(c)) and is similar to 0.733 nm of BHJ surface (FIG. 6(a)). ETL-1 on BHJ exhibited a RMS of 1.01 nm with relatively rough surface (FIG. 6(b)).

In one aspect, the invention provides representative fullerene surfactants, ETL-1 and ETL-2, which can be readily processed in orthogonal solvents (e.g., methanol) on a BHJ layer in PSCs. These materials possess proper electron mobility and the capability of tuning cathode Φ to improve electron extraction and photocurrent generation. Upon the insertion of a thin ETL-1 or ETL-2 between various metal cathodes and BHJ layer (device A-I), simultaneously improved $V_{OC}$, $J_{SC}$ and FF could be achieved for these devices compared to those without using surfactant. The performance of PSCs is significantly improved (70% for Al cathode and 40% for Ag cathode) when surfactant-modified cathode was applied. High performance PSCs using fullerene ETL modified Ag cathode were realized (as high as 6.63%) which is superior to those of Ca/Al and Al based devices.

Figure 7:
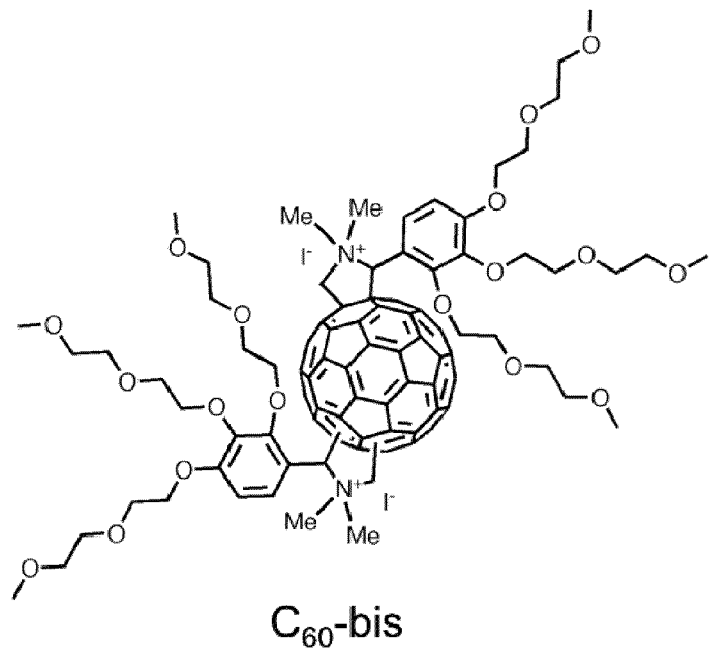
FIG. 7 shows the chemical structure of a representative fullerene surfactant of the invention: ETL-2 ("$C_{60}$-bis").
Figure 8A:
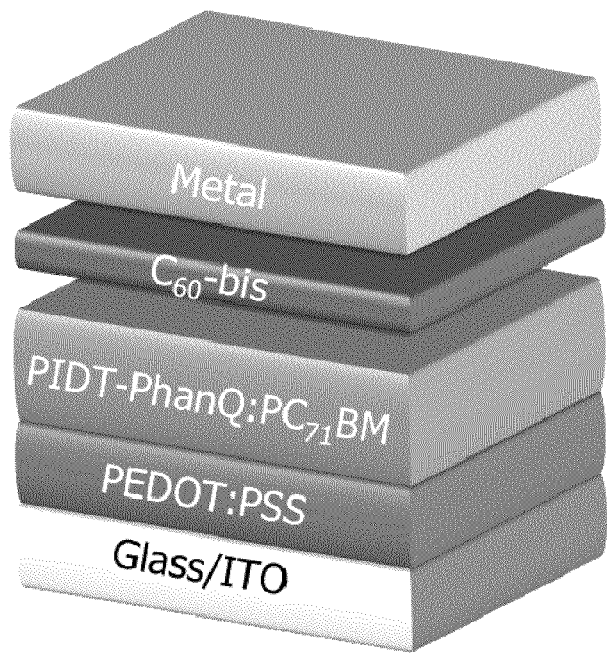
FIG. 8A is a schematic illustration of the architecture of a representative photovoltaic device of the invention.
Figure 8B:
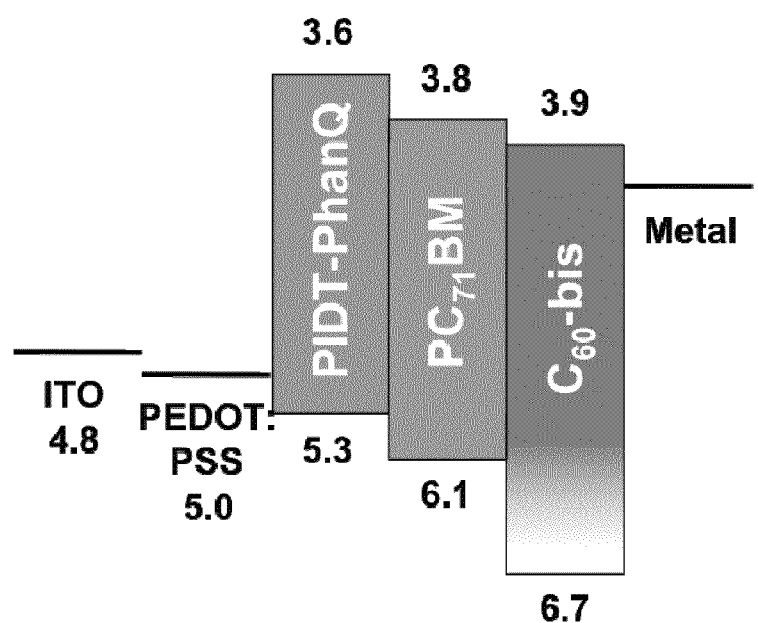
FIG. 8B is a schematic illustration of the energy level diagram of the device of FIG. 8A.

The following is a description of the use of a representative fullerene surfactant of the invention, ETL-2 ("$C_{60}$-bis") (FIG. 7), in an interfacial layer to enhance the efficiency of polymer solar cells. FIG. 8A is a schematic illustration of the architecture of a representative photovoltaic device of the invention. FIG. 8B is a schematic illustration of the energy level diagram of the device of FIG. 8A.

Devices were fabricated with higher WF metals less prone to oxidation, which are shown to perform better than Al devices over time. Remarkably, the $V_{OC}$ appears to be independent of the choice of cathode metal when $C_{60}$-bis is used as a buffer layer.

Figure 9A:
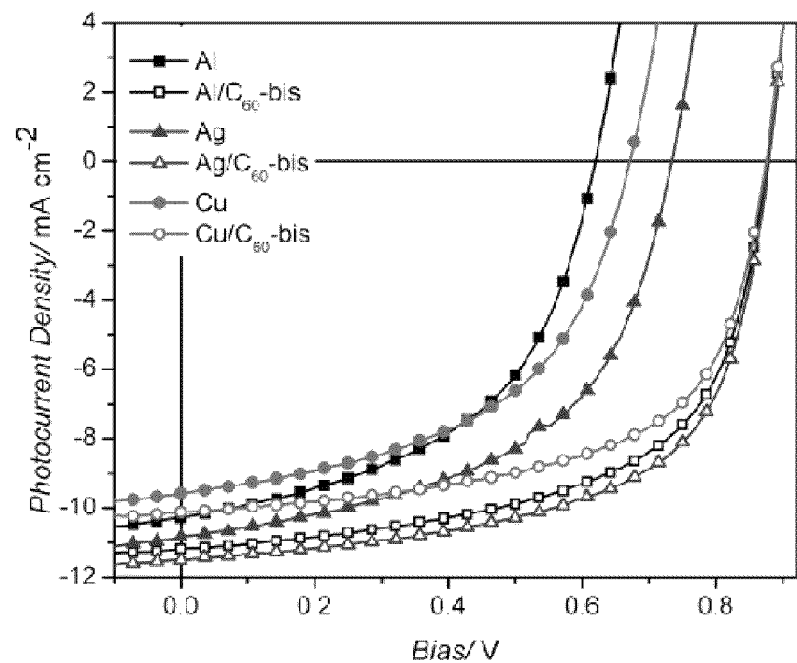
FIGS. 9A-9D compare performance data for PIDT-PhanQ:$PC_{71}BM$ devices fabricated with different choice of cathode metal with and without a $C_{60}$-bis interlayer. The current density-voltage curves (9A) and external quantum efficiency spectra (9B) show increases in $V_{OC}$ and $J_{SC}$ respectively. Capacitance-voltage (9C) and Mott-Schottky (9D) analysis explain increased $V_{OC}$ in terms of the $V_{BI}$ of the Schottky contact.

FIG. 9A shows the J-V characteristics for devices fabricated with different cathode metals both with and without a $C_{60}$-bis buffer layer. The $V_{OC}$ for devices with an Al cathode is consistently lower than that of Cu and Ag devices, which can be attributed to the rapid oxidation of Al in air. The non-ideal nature of this interface also manifests in a modest fill factor (FF) of 0.51 and an overall PCE of 3.22%. In contrast, when a layer of $C_{60}$-bis is used, the PCE increases to 5.87% as a result of an increase in $J_{SC}$, FF and most notably $V_{OC}$. In addition, the shunt resistance is shown to increase for all metals in the case of $C_{60}$-bis, which provides evidence of lower leakage current under illumination. Performance data for all devices are summarized in Table 3.

TABLE 3

Performance data for PIDT-PhanQ:$PC_{71}BM$ devices with different cathode metals, with and without $C_{60}$-bis.

| Device | $V_{OC}$ [V] | $J_{SC}$ [mA cm$^{-2}$] | FF | PCE [%] | $R_{SH}$ [Ωcm$^{-2}$] |
|---|---|---|---|---|---|
| Al | 0.62 | 10.28 | 0.51 | 3.22 | 309.33 |
| Al/$C_{60}$-bis | 0.88 | 11.19 | 0.60 | 5.87 | 773.33 |
| Ag | 0.73 | 10.83 | 0.53 | 4.22 | 351.63 |
| Ag/$C_{60}$-bis | 0.88 | 11.50 | 0.61 | 6.22 | 662.86 |
| Cu | 0.67 | 9.58 | 0.51 | 3.32 | 386.67 |
| Cu/$C_{60}$-bis | 0.87 | 10.13 | 0.61 | 5.37 | 795.43 |

Figure 9B:
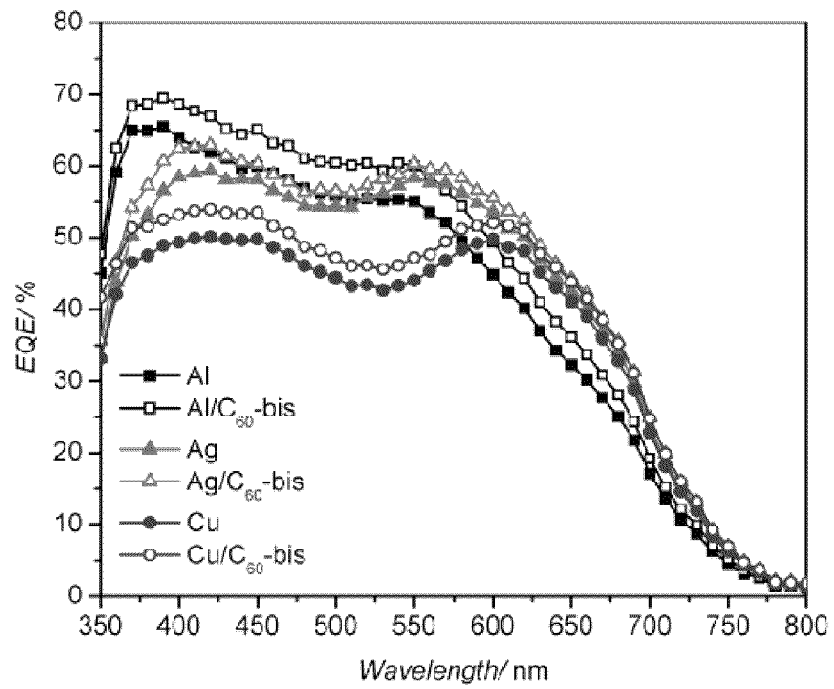

To investigate the improvement in $J_{SC}$, external quantum efficiency (EQE) spectra (FIG. 9B) were obtained for Al, Ag, and Cu devices. The spectra exhibit an almost constant increase across the entire wavelength range for each case when the surfactant layer was inserted. This indicates the improvement in $J_{SC}$ is due entirely to the inclusion of the surfactant and a concurrent decrease in recombination resistance at the organic/electrode interface, rather than a change in bulk morphology.

Figure 10:
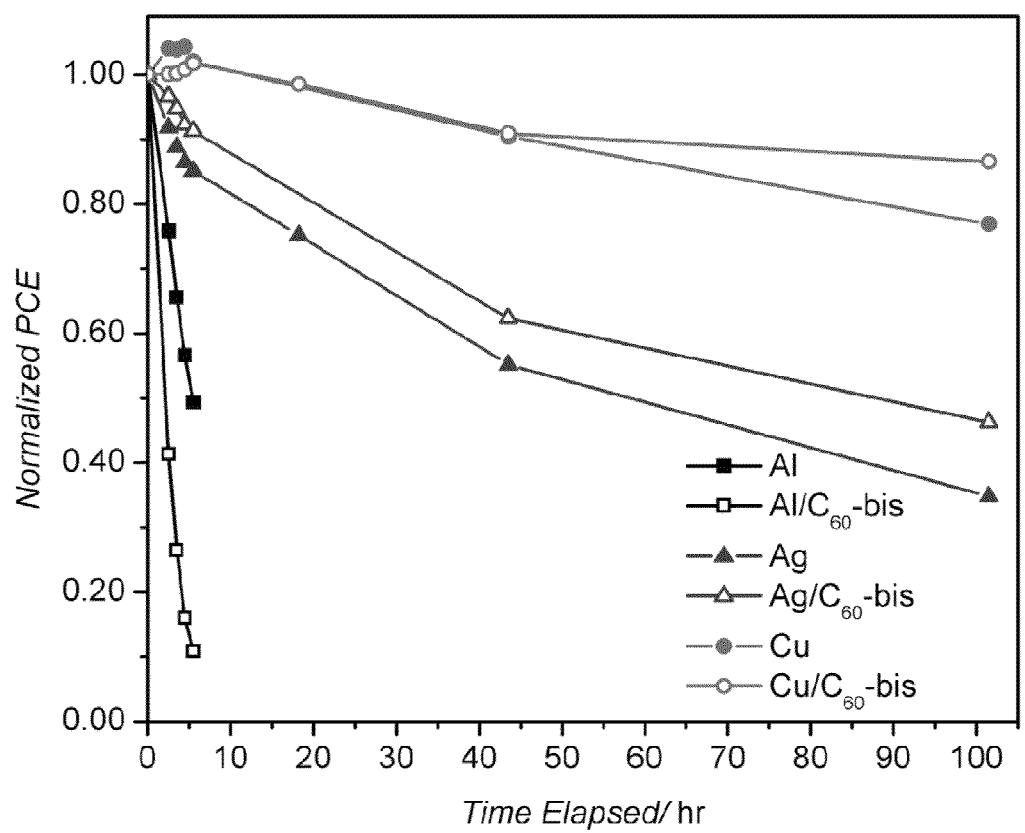
FIG. 10 compares normalized PCE for Al, Ag, and Cu devices with and without $C_{60}$-bis under ambient conditions.

To further demonstrate the utility of $C_{60}$-bis as an interfacial layer, the PCE of devices with different cathode metals were tracked over a period of time under exposure to ambient conditions. FIG. 10 shows the normalized PCE for unencapsulated devices with and without $C_{60}$-bis over 100 h in air. As expected the performance of Al devices drops off rapidly, even with the inclusion of the fullerene surfactant, which is likely due to the uptake of oxygen and water molecules and their subsequent diffusion to the metal/organic interface. The Ag and Cu devices remain very stable, however, with the Cu/$C_{60}$-bis retaining nearly 90% of its original PCE after the entire period of ambient exposure.

By far the most obvious benefit of $C_{60}$-bis is a strongly enhanced $V_{OC}$. To further investigate the dramatic increase in $V_{OC}$ when $C_{60}$-bis is used, capacitance-voltage characteristics (C-V) were obtained and devices were analyzed via Mott-Schottky (MS) analysis. It has previously been shown that, due to the intrinsic p-doped nature of semiconducting polymers, a Schottky contact is formed upon deposition of the cathode onto the photoactive layer. The depletion zone formed at this interface is modulated by the applied voltage under reverse and low (<1.5V) forward bias. Band-bending has been shown to result in the vicinity of the cathode, allowing extraction of the built-in potential ($V_{BI}$) and impurity concentration (N) of the region by application of $C^{-2} = (2/q \in N)(V_{BI} - V)$ to the appropriate bias voltage range.

Figure 9C:
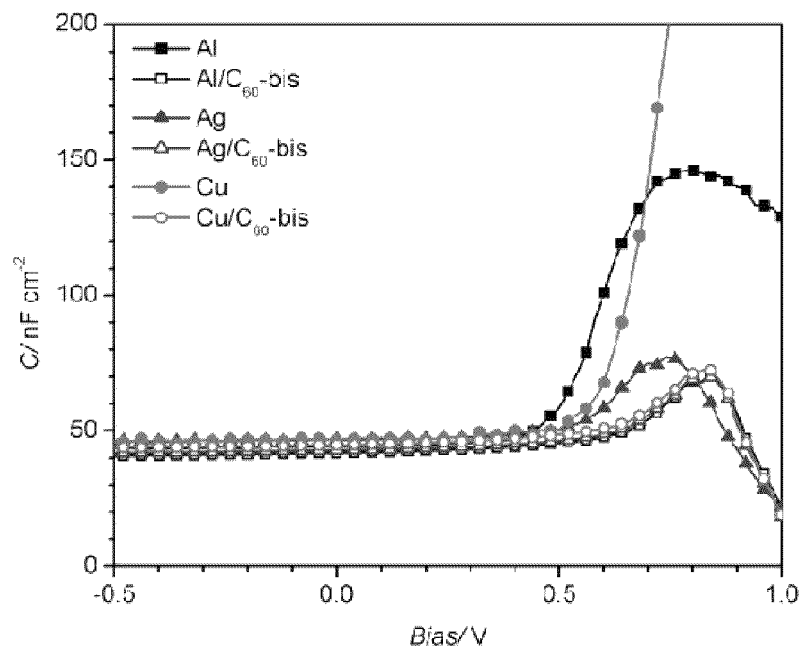
Figure 9D:
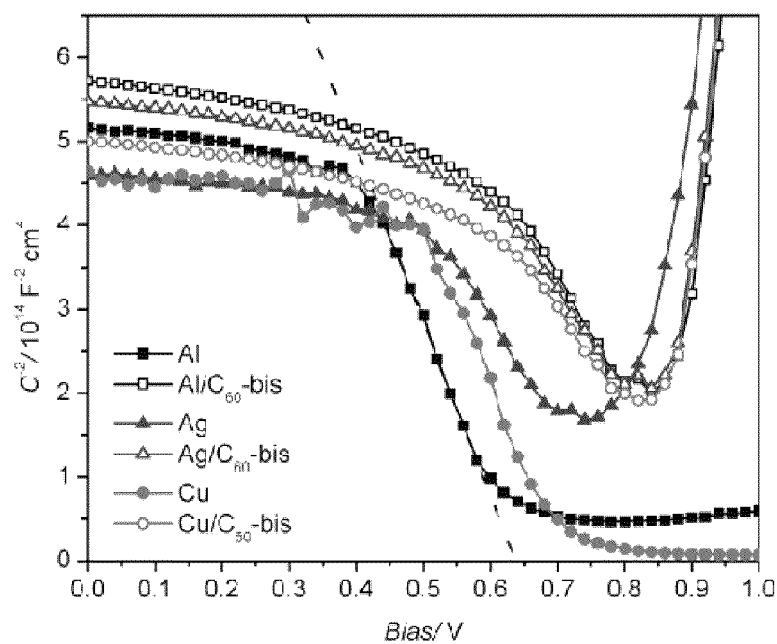

FIG. 9C shows the capacitance behavior of all devices as a function of bias voltage. The low capacitance region up to about 0.5 V has been attributed to the capacitance of the depletion layer, whereas a further increase in forward bias voltage yields a peak in the capacitance related to the storage of minority carriers in the bulk. FIG. 9D shows the MS plot for all fabricated devices. At moderate to high reverse bias, $C^{-2}$ tends to reach a steady value related to the geometric capacitance of the organic material which has become fully depleted of majority carriers and can be viewed as a classical dielectric. The linear region under low forward bias is related to the formation of a Schottky contact and can be fitted to a plot of $C^{-2}$ versus bias voltage. Extrapolation of the linear fit line to the intercept on the bias axis directly yields $V_{BI}$ for the device. Once a value for $V_{BI}$ has been obtained, an impurity concentration N and depletion width $w = (2 \in V_{BI}/qN)^{1/2}$ corresponding to zero applied bias can be extracted. A dielectric permittivity of 3 has been assumed for calculations involving these equations. MS analysis data, along with the relative shifts in $V_{OC}$ and $V_{BI}$, are summarized in Table 4.

TABLE 4

Built-in potential $V_{BI}$, dopant concentration N, and depletion width w of the organic/cathode Schottky contact from Mott-Schottky analysis. The work functions and relative shifts in $V_{OC}$ and $V_{BI}$ for all devices are also included.

| Device | $V_{OC}$ [V] | $V_{BI}$ [V] | ($\Delta V_{OC}$, $\Delta V_{BI}$) [V] | N [$10^{16}$ cm$^{-3}$] | w [nm] | $\Phi_{cathode}$ [eV] |
|---|---|---|---|---|---|---|
| Al | 0.619 | 0.636 | — | 2.25 | 97 | 4.25 |
| Al/$C_{60}$-bis | 0.877 | 0.940 | (0.26, 0.30) | 3.32 | 97 | 3.66 |
| Ag | 0.734 | 0.808 | — | 3.39 | 89 | 4.57 |
| Ag/$C_{60}$-bis | 0.879 | 0.959 | (0.15, 0.15) | 3.77 | 92 | 3.97 |
| Cu | 0.672 | 0.712 | — | 2.51 | 97 | 4.70 |
| Cu/$C_{60}$-bis | 0.875 | 0.957 | (0.20, 0.25) | 4.02 | 89 | 3.96 |

The depletion width extracted from the capacitance-voltage data extends over almost the entire thickness of the active layer. When taken with the N values obtained from the same data, this indicates a consistent doping profile across the entire layer that changes negligibly by inclusion of $C_{60}$-bis. Because the change in the Fermi level of the active layer ($E_F^P$) can be approximated by $\Delta E_F^P = k_b T \ln(N_b/N_a)$, where $N_b$ and $N_a$ are the dopant concentrations of the device with and without $C_{60}$-bis, respectively, it is reasonable to conclude that $E_F^P$ does not change more than ca. 10 meV. When a semiconductor is placed in intimate contact with a metal, their respective $E_F$ come into equilibrium by electrons being transferred "downhill" in energy. Referencing $V_{BI}$ to $E_F^P$ by $V_{BI} = (E_F^P -$ $\Phi_{cathode}$), where $\Phi_{cathode}$ is the cathode WF, then the difference in $V_{BI}$ with and without $C_{60}$-bis can be attributed to a modification of $\Phi_{cathode}$ by the surfactant. Furthermore, because the relative shifts in $V_{BI}$ closely follow those of $V_{OC}$ for all three metals we can conclude that the observed increase in $V_{OC}$ upon inclusion of $C_{60}$-bis is due to a dipole-induced shift in $\Phi_{cathode}$ at the interface.

Figure 12A:
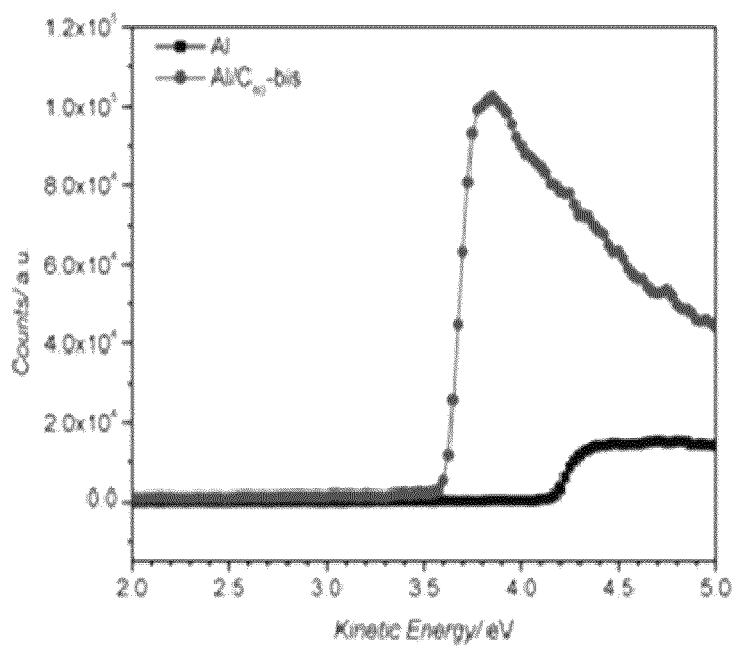
FIGS. 12A-12C compare secondary electron cutoff spectra of Al (12A), Ag (12B), and Cu (12C) metal films with and without $C_{60}$-bis. Films without $C_{60}$-bis were $Ar^+$ sputter-cleaned in vaccuo prior to measurement. The Cu spectrum includes that of clean Au foil as a reference.
Figure 12B:
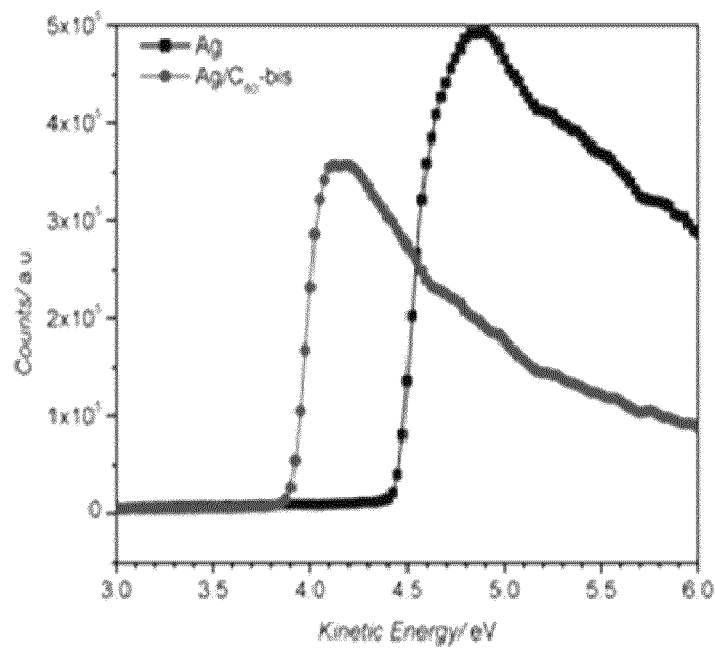
Figure 12C:
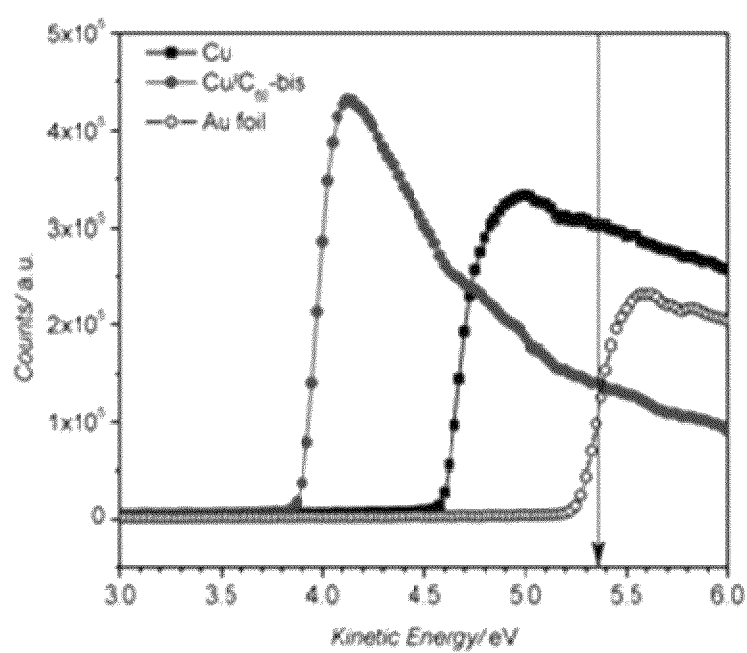

To further investigate the energetics at the interface, WFs were obtained for Al, Ag, and Cu with and without $C_{60}$-bis spin-coated on top and are summarized in Table 4. WFs of in-situ, sputter-cleaned Al, Ag, and Cu films were measured to be 4.25 eV, 4.57 eV and 4.70 eV, respectively (FIGS. 12A-12C). The WFs of Ag and Cu with $C_{60}$-bis yield nearly the same value. Because sampling of the substrate at normal emission is highly surface sensitive, it is reasonable to assume these WF values correspond to the $C_{60}$-bis. As the material is an n-type semiconductor, one would expect $E_F$ to be closer to the LUMO level than mid-gap. It should be noted that the WFs of the organic overlayer may not be measured in the flat-band condition, but are rather subject to any band bending occurring at the metal/organic interface as a result of $E_F$ equilibration. Additionally, it is likely that an unavoidable thin oxide layer formed on the Al sample when it was removed from the glovebox for $C_{60}$-bis deposition, as evidenced by a comparison of O1s peak intensity in XPS survey spectra for bare Al before and after sputter-cleaning with Ar$^+$ ions. These considerations might explain the lower WF of the modified Al cathode as compared to Ag and Cu.

It should be stressed that these conditions do not prevail for regular device fabrication since the cathode is deposited under high vacuum after spin-coating the $C_{60}$-bis layer outside the glovebox. Regardless, at a distance sufficiently far into the bulk of the photoactive layer only the effective WF of the $C_{60}$-bis modified cathode can be seen by the rest of the device. This ensures a constant difference between $E_F^P$ and $\Phi_{cathode}$, and explains why $V_{BI}$, and consequently $V_{OC}$, is nearly the same for all three metals when $C_{60}$-bis is employed.

A $C_{60}$ bis-adduct surfactant was used to modify the energy level alignment at the organic/cathode interface in conventional structure, bulk-heterojunction OSC devices. A well-defined interface between the photoactive layer and the surfactant was ensured by virtue of process solvent orthogonality. The large increase in device $V_{OC}$ is independent of the choice of cathode metal due to pinning of the metal $E_F$ to that of the $C_{60}$-bis upon equilibration. Mott-Schottky analysis of the interface formed between the photoactive layer and the cathode yields a built-in potential defined by the difference between the Fermi level of the bulk-heterojunction $E_F^P$ and the effective cathode work function $\Phi_{cathode}$. The observed changes in $V_{BI}$ are reflected in the magnitude of the change in $V_{OC}$. Further, EQE data reveal the overall device performance enhancement to be due entirely to the inclusion of the surfactant, rather than a beneficial change in photoactive layer morphology.

The following examples are provided for the purpose of illustrating, not limiting, the invention.

EXAMPLES

Example 1

The Preparation, Characterization, and Use of Representative Fullerene Surfactants: ETL-1 and ETL-2

In this example, the preparation, characterization, and use of representative fullerene surfactants, ETL-1 and ETL-2, is described. The fabrication and characterization of devices that include the surfactants is also described.

All reactions dealing with air- or moisture-sensitive compounds were carried out using standard Schlenk technique. All $^1$H (500 MHz) and $^{13}$C (125 MHz) spectra were recorded on Bruker AV500 spectrometers. Spectra were reported in parts per million from internal tetramethylsilane ($\delta$0.00 ppm) or residual protons of the deuterated solvent for $^1$H NMR and from solvent carbon (e.g., $\delta$77.00 ppm for chloroform) for $^{13}$C NMR. The matrix for MALDI-TOF-MS used 2:1 mixture of alpha-cyano-4-hydroxycinnamic acid (CHCA)/2,5-dihydroxybenzoic acid (DHB) in acetonitrile. Elemental analyses were performed by QTI, Whitehouse, N.J. (www.qtionline.com). AFM images under tapping mode were taken on a Veeco multimode AFM with a Nanoscope III controller. 2,3,4-Tris(2-(2-methoxyethoxy)ethoxy)benzaldehyde and fulleropyrrolidines were synthesized according to literature methods (Benzaldehyde: Nielsen, C B.; Johnsen, M.; Arnbjerg, J.; Pittelkow M.; McIlroy, S P.; Ogilby, P R.; Jrgensen, M. *J Org. Chem.* 2005, 70:7065. Fulleropyrrolidines and fulleropyrrolidiums: Bosi, S.; Feruglio, L.; Milic, D.; Prato, M. *Eur. J. Org. Chem.* 2003, 4741). $C_{60}$ was purchased from American Dye Source. Unless otherwise noted, materials were purchased from Aldrich Inc., and used after appropriate purification.

Synthesis of Fulleropyrrolidiums

A solution of $C_{60}$ (300 mg, 0.35 mmol), 2,3,4-tris(2-(2-methoxyethoxy)ethoxy)benzaldehyde (478 mg, 1.04 mmol) and sarcosinic acid (111 mg, 1.25 mmol) in chlorobenzene (100 mL) was refluxed under $N_2$ for 4 h. After evaporation of the solvent, the residue was subjected to chromatograph purification on a silica gel column. Elution with toluene gave little unchanged $C_{60}$. Fraction containing mono adduct was collected with PhMe/EtOAc (1:2) eluent. One fraction of bisadducts consisting mixture of regioisomers was then collected with EtOAc eluent. Each sample was precipitated from toluene solution with methanol or hexane, and gave monofulleropyrrolidine (115 mg, 27%), bisfulleropyrrolidine (90 mg, 15%).

Quaternization of neutral fulleropyrrolidines was achieved by heating a solution of mono or bis fulleropyrrolidine (0.05 mmol) in chloroform (2 mL) and MeI (1.5 mL) in a screw-topped Schlenk tube under $N_2$. Reaction mixture was kept at 80° C. for 40 h. After evaporation of the solvent, the product was dissolve in chloroform and precipitated with hexane. After thoroughly washed with n-hexane, black fulleropyrrolidiums, ETL-1 or ETL-2, were obtained in quantitative yield.

Monofulleropyrrolidine.

$^1$H NMR (500 MHz, CDCl$_3$): $\delta$2.78 (s, 3H, NCH$_3$), 3.34 (s, 3H, OCH$_3$), 3.36 (s, 3H, OCH$_3$), 3.40 (s, 3H, OCH$_3$), 3.48-3.50 (m, 2H, OCH$_2$), 3.53-3.58 (m, 4H, OCH$_2$), 3.63-3.80 (m, 10H, OCH$_2$), 3.86 (t, J=5.5 Hz, 2H, OCH$_2$), 3.05-4.18 (m, 4H, OCH$_2$), 4.27-4.32 (m, 2H, OCH$_2$), 4.37-4.40 (m, 2H, OCH$_2$), 4.94 (d, J=9.5 Hz, 1H, NCH$_2$), 5.56 (s, 1H, NCH$_2$), 6.77 (d, J=8.5 Hz, 1H, Ar—H), 7.63 (d, J=8.5 Hz, 1H, Ar—H). $^{13}$C NMR (125 MHz, CDCl$_3$): $\delta$39.89, 58.99, 59.00, 59.03, 59.05, 59.18, 59.19, 68.36, 69.25, 69.76, 69.83, 70.21, 70.35, 70.62, 70.72, 70.74, 71.95, 71.98, 72.05, 72.23, 73.18, 75.74, 77.20, 109.34, 123.31, 124.57, 134.82, 136.06, 136.49, 136.59, 139.47, 139.53, 140.12, 140.14, 141.19, 141.58, 141.67, 141.89, 141.99, 142.08, 142.11, 142.16, 142.28, 142.29, 142.54, 142.57, 142.63, 142.65, 143.00, 143.08, 144.36, 144.45, 144.61, 145.11, 145.12, 145.18, 145.23, 145.26, 145.31, 145.55, 145.76, 145.94, 146.07, 146.09, 146.12, 146.20, 146.27, 146.77, 146.95, 147.30, 152.20, 152.47, 154.15, 154.33, 155.16, 156.87. MALDI-TOF-MS (+): calcd. for [C$_{84}$H$_{41}$NO$_9$]−, 1208.225, found. [M]⁻, 1207.893.

Bisfulleropyrrolidine.

$^1$H NMR (500 MHz, CDCl$_3$): δ2.55-2.88 (m, NCH$_3$), 3.29-3.40 (m, OCH$_3$), 3.42-4.00 (m, OCH$_2$&OCH$_3$), 4.06-4.68, 4.92-5.57, 5.74-5.75, 6.52-6.98, 7.35-7.49, 7.59-7.69, 7.73-7.88, 8.00-8.03; $^{13}$C NMR (125 MHz, CDCl$_3$): δ39.66-39.83 (m, NCH$_3$), 53.21-53.43 (m), 58.97-59.22 (m), 68.17-68.43, 69.42, 69.70-69.94, 70.14-70.91, 71.90-72.35, 72.92-73.50, 75.34-76.00, 77.40-77.66, 109.12-109.48, 123.58-123.98, 124.42-124.61, 134.87, 136.53, 139.39, 140.76-141.93, 142.14, 142.00, 142.23, 142.30, 142.37, 142.51, 142.58, 142.95, 142.97, 143.38, 143.39, 143.58, 144.12, 144.36, 144.85, 144.96, 145.08, 145.21, 145.26, 145.44-145.74, 146.05, 146.07, 147.25, 147.47, 147.72, 147.84, 148.64, 148.77, 149.03, 150.75-151.39, 151.97-152.83, 153.66, 154.28-154.98, 155.54; MALDI-TOF-MS (+): calcd. for [C$_{108}$H$_{82}$N$_2$O$_{18}$], 1695.809, found. [M-I]$^+$, 1695.929.

Fulleropyrrolidium ETL-1.

$^1$H NMR (500 MHz, CDCl$_3$): δ3.36 (s, 3H, OCH$_3$), 3.38 (s, 3H, OCH$_3$), 3.52-3.56 (m, 7H, OCH$_2$&OCH$_3$), 3.67-3.77 (m, 8H, OCH$_2$), 3.80-3.84 (m, 2H, OCH$_2$), 3.89 (m, 2H, OCH$_2$), 3.97 (s, 3H, NCH$_3$), 4.02 (d, J=8.5 Hz, 2H, OCH$_2$), 4.20-4.39 (m, 4H, OCH$_2$), 4.48 (s, 3H, NCH$_3$), 4.66-4.68 (m, 2H, OCH$_2$), 5.80 (d, J=12.5 Hz, 1H, NCH$_2$), 6.84 (d, J=13.0 Hz, 1H, NCH$_2$), 6.88 (d, J=9.0 Hz, 1H, Ar—H), 7.28 (d, J=13.0 Hz, 1H, NCH$_2$), 7.71 (d, J=8.5 Hz, 1H, Ar—H); $^{13}$C NMR (125 MHz, CDCl$_3$): δ45.69, 53.44, 59.04, 59.07, 59.08, 59.28, 67.89, 68.44, 69.38, 69.96, 70.43, 70.54, 70.69, 70.72, 71.42, 71.65, 71.93, 71.97, 72.53, 72.56, 73.13, 73.64, 78.60, 108.66, 111.57, 127.48, 134.10, 134.75, 135.52, 136.11, 139.03, 139.87, 139.98, 140.26, 140.93, 141.24, 141.38, 141.43, 141.45, 141.62, 141.82, 142.03, 142.09, 142.11, 142.13, 142.35, 142.39, 142.51, 142.52, 142.76, 142.84, 142.96, 143.01, 143.12, 143.33, 144.19, 144.23, 144.36, 144.42, 144.82, 144.89, 145.14, 145.26, 145.30, 145.45, 145.54, 145.61, 145.66, 145.77, 145.82, 145.96, 146.02, 146.13, 146.18, 146.35, 146.40, 147.42, 147.56, 149.32, 150.51, 151.18, 152.66, 153.66, 153.83, 155.77; MALDI-TOF-MS (+): calcd. for [C$_{85}$H$_{44}$NO$_9$]$^+$·I$^-$, 1350.16, found. [M-I]$^+$, 1222.144; Anal. Calcd for C$_{85}$H$_{44}$INO$_9$: C, 75.61; H, 3.28; N, 1.04. Found: C, 73.29; H, 2.76; N, 0.76.

Fulleropyrrolidium ETL-2 (Mixture of Regioisomers).

$^1$H NMR (500 MHz, CDCl$_3$/CD$_3$OD): δ3.32-3.40 (m, OCH$_3$), 3.42-4.03 (m, OCH$_2$&OCH$_3$), 4.12-4.50 (m, OCH$_2$), 4.56-4.61 (m, OCH$_2$), 4.70-4.72 (m, OCH$_2$), 5.36-5.69 (m, NCH$_2$), 6.02-6.07, 6.68-6.97, 7.04-7.13, 7.20-7.21, 7.32-7.34, 7.37-7.61, 7.77-7.89, 7.98-8.04, 8.10-8.14, 8.27-8.31; $^{13}$C NMR (125 MHz, CDCl$_3$): δ45.28-46.47 (m), 53.21-53.43 (m), 58.99-59.49 (m), 66.06, 66.83, 68.45, 68.49-69.41, 69.51-70.89, 71.27-71.52, 71.96-72.06, 72.46-72.67, 73.55-73.84, 78.65, 78.75, 109.24, 109.35, 109.48, 111.29, 111.44, 136.24, 136.67, 140.04, 140.44, 140.84, 140.96, 141.13, 141.35, 141.58, 141.60, 141.67, 141.73, 141.77, 141.81, 141.83, 141.94, 142.14, 142.17, 142.21, 142.32, 142.38, 142.40, 142.51, 142.61, 145.38, 145.48, 145.59, 146.14, 146.20, 147.21, 147.40, 147.53, 147.79, 147.96-148.09, 148.40, 148.70-148.82, 149.08-149.32, 150.06, 151.57, 153.67-153.76, 155.68-155.89; MALDI-TOF-MS: calcd. for [C$_{110}$H$_{88}$N$_2$O$_{18}$]$^{2+}$·2I$^-$, 1979.69, found [M-2I-NMe$_3$]$^+$ 1666.278; Anal. Calcd for C$_{110}$H$_{88}$I$_2$N$_2$O$_{18}$: C, 66.74; H, 4.48; N, 1.42. Found: C, 66.07; H, 4.23; N, 1.35.

CV Measurements

Cyclic voltammetry (CV) measurements were carried out in a one-compartment cell under N$_2$, equipped with a glassy-carbon working electrode, a platinum wire counter electrode, and an Ag/Ag$^+$ reference electrode. Measurements were performed in THF solution containing tetrabutylammonium hexafluorophosphate (0.1 M) as a supporting electrolyte with a scan rate of 100 mV/s. All potentials were corrected against Fc/Fc$^+$. Due to close vicinity of the electron-deficient cationic nitrogen to the fullerene core, the LUMO level of ETL-1 to that of ETL-2 has a small difference in 0.03 eV.

Fabrication and Characterization of PSCs

[6,6]-Phenyl-C61 (or C71)-butyric methyl ester was purchased from American Dye Source. PEDOT:PSS (Baytron P VP AI 4083) was purchase from H. C. Stark. Materials were used as received. The fullerene surfactant solutions in methanol were sonicated for 2 hrs prior to spin-coating in ambient at 5000 RPM. The surfactant layer thickness was about 8-10 nm as measured by AFM. The ITO substrates were cleaned by ultrasonication in acetone for 15 min, followed by manual scrubbing with detergent and deionized water, then sonication in deionized water and isopropanol for 15 min each. The substrates were blown dry under a nitrogen stream and immediately exposed to air plasma for 20 seconds. A 40 nm thick layer of PEDOT:PSS was spin coated onto each substrate and subsequently annealed in air at 140° C. for 30 min. The mixture of PIDT-PhanQ:PC$_{71}$BM in o-dichlorobenzene (20 mg/ml, 1:3, w:w) was then spin-coated on the PEDOT:PSS layers at 800 RPM, and subsequently annealed at 110° C. for 10 min under nitrogen atmosphere to obtain a film thickness approximately 80 nm. After fullerene surfactant solutions was spin coated on the BHJ layer. The substrates were then transferred back into the glovebox and annealed at 110° C. for 5 min. Finally, aluminum (100 nm) or calcium (30 nm) topped with aluminum (100 nm), or silver (100 nm) was thermally evaporated onto the active layer through shadow masks.

Photocurrent-voltage (J-V) measurements were performed using a Keithley 4200 in a nitrogen-filled glove box under AM1.5 illumination conditions at intensity of 100 mW/cm$^2$. A NREL certified silicon photodiode with a KG5 filter was used to calibrate. Device EQE spectra were obtained in air by comparison to a known AM1.5 reference spectrum for a calibrated silicon photodiode.

Organic Field-Effect Transistors

Top contact OFETs were fabricated as typical top contact, bottom gate devices on silicon substrates. Heavily doped p-type silicon <100> substrates from Montco Silicon Technologies INC. with a 300 nm (±5 nm) thermal oxide layer acted as a common gate with a dielectric layer. After cleaning the substrate by sequential ultrasonication in acetone, methanol, and isopropyl alcohol for 15 min flowed by air plasma treatment, the different fullerene surfactant films were spin-coated from a 0.5 wt % chloroform solution in ambient. Interdigitated source and drain electrodes (W=1000 μm, L=12 μm) were defined by evaporating a 50 nm Au film through a shadow mask from the resistively heated Mo boat at 10$^{-6}$ Torr. OFET characterization was carried out in a N$_2$-filled glovebox using an Agilent 4155B semiconductor parameter S6 analyzer. The field-effect mobility was calculated in the saturation regime from the linear fit of $(I_{ds})_{1/2}$ vs $V_{gs}$. The threshold voltage ($V_t$) was estimated as the x intercept of the linear section of the plot of $(I_{ds})_{1/2}$ vs $V_{gs}$. The sub threshold swing was calculated by taking the inverse of the slope of $I_{ds}$ vs $V_{gs}$ in the region of exponential current increase.

Work Function Measurements by XPS

Samples for work function analysis were prepared on glass substrates coated with ITO to ensure good electrical contact. Work functions were measured with a PHI Versa Probe X-ray photoelectron spectrometer (ULVAC-PHI, Kanagawa, Japan) employing a monochromatic focused Al—Kα X-ray source and hemispherical analyzer. The Au 4f$_{7/2}$ (84.00 eV) and Cu 2p$_{3/2}$ (932.66 eV) photoemission peaks were used to calibrate the binding energy scale. A bias voltage (−5 V) was applied to the sample, and the location of the secondary electron cut-off was determined at normal emission by a linear extrapolation to the background level. To account for the instrument width, 0.14 eV were added to the work function values thus obtained. This procedure gives a work function for argon ion sputtered gold foil of 5.17 eV.

TABLE 5

Comparison of WF of cathodes.

|  | Al | ETL-1/Al | ETL-2/Al |
|---|---|---|---|
| Secondary electron emission (eV) | 1477.54 | 1478.16 | 1478.32 |
| Work-Function (eV) | 4.20 | 3.66 | 3.42 |

Example 2

The Preparation and Characterization of Representative Photovoltaic Devices with Fullerene Surfactant-Containing Interfacial Layer In this example, the preparation and characterization of representative photovoltaic devices with a fullerene surfactant-containing layer intermediate the active layer and cathode is described.

Fabrication of Photovoltaic Devices

ITO-coated glass substrates (15Ω sq$^{-1}$) were cleaned sequentially by sonication in detergent and deionized water, acetone and isopropanol. After drying under a $N_2$ stream, substrates were air-plasma treated for 30 s. A about 35 nm layer of PEDOT:PSS (Baytron® P VP Al 4083, filtered through a 0.45 μm nylon filter) was spin-coated onto the clean substrates at 5 kRPM and annealed at 140° C. for 10 min. The substrates were transferred to a $N_2$-filled glovebox where a homogeneously blended solution of PIDTPhanQ:PC$_{71}$BM (40 mg/ml in o-dichlorobenzene stirred overnight in glovebox, 1:3 polymer:fullerene by weight) was spin-coated at 2 k RPM, producing an active layer about 100 nm thick, and annealed at 110° C. for 10 min. Substrates requiring a layer of fullerene surfactant were briefly transferred out of the glovebox (total ambient exposure <10 min) and about 2-5 nm thick film of $C_{60}$-bis surfactant (1 mg/ml in methanol) was spin-coated at 5 k RPM. The substrates were then transferred back into the glovebox and annealed at 110° C. for 5 min to drive off any remaining solvent prior to metal deposition. Metal electrodes were deposited at a base pressure <1×10$^{-6}$ Torr through a shadow mask, defining an active device area of 4.64 mm$^2$. Ag and Cu were deposited at a rate of 1 Å s$^{-1}$ and Al was deposited at a rate of 4 Å s$^{-1}$.

Preparation of XPS Samples

ITO-coated glass substrates were prepared as above without air-plasma treatment. Al, Ag, and Cu were deposited over the entire substrate surface at a rate of 1 Å s$^{-1}$. Substrates requiring a thin layer of fullerene surfactant were transferred out of the glovebox and a solution of $C_{60}$-bis surfactant was spin-coated from methanol using the same conditions as above. After transfer back into the glovebox, all substrates were heated at 70° C. for 5 min to evaporate any remaining methanol prior to being sealed with parafilm in 20 ml glass vials under $N_2$ for transport to the XPS.

Measurement and Characterization

J-V characteristics of the unencapsulated devices were measured in ambient conditions using a Keithley 2400 source meter under AM 1.5 G (100 mW cm$^{-2}$) irradiation simulated by an Oriel xenon lamp (450 W). AM 1.5 G illumination was confirmed by means of calibration to a standard silicon photodiode (Hammamatsu) which can be traced to the National Renewable Energy Laboratory. External quantum efficiency spectra were obtained by measuring the photocurrent response of the device using chopped, monochromated light from the same xenon lamp in conjunction with a Stanford Research Systems SR830 lock-in amplifier under ambient conditions. Mott-Schottky analysis was performed in a $N_2$-filled glovebox in the dark using a Signatone probe station interfaced with a Hewlett-Packard HP4284A LCR meter. The 1 kHz AC field applied during measurement was kept at an amplitude of 25 mV to maintain response linearity. Capacitance-voltage characteristics measured thusly were obtained using devices prepared as above with an active area of 10.08 mm$^2$. Work function determination via XPS is described below. Briefly, the secondary electron cutoff (SEC) spectrum of each sample was measured under ultra-high vacuum (<5× 10$^{-9}$ Torr) using a PHI 5000 VersaProbe (Ulvac-Phi, Inc.) employing a focused, monochromated Al K-α x-ray source and a hemispherical analyzer. Proper referencing of the SEC edge to that of Ar$^+$ ion sputter-cleaned, polycrystalline gold allowed for accurate determination of the sample work functions with a reproducibility of about 0.05 eV.

Cyclic Voltammetry Measurements

Cyclic voltammetry measurements were carried out under $N_2$ in a one-compartment cell equipped with a glassy carbon working electrode, a platinum wire counter electrode, and an Ag/Ag$^+$ reference electrode. Measurements were performed in THF solution containing tetrabutylammonium hexafluorophosphate (0.1 M) as a supporting electrolyte with a scan rate of 100 mV/s. All potentials were corrected against the Fc/Fc$^+$ couple and LUMO levels were estimated using the following equation: LUMO=−(4.8+$E_{1/2}^{red1}$)eV.

Work Function Determination

Figure 11:
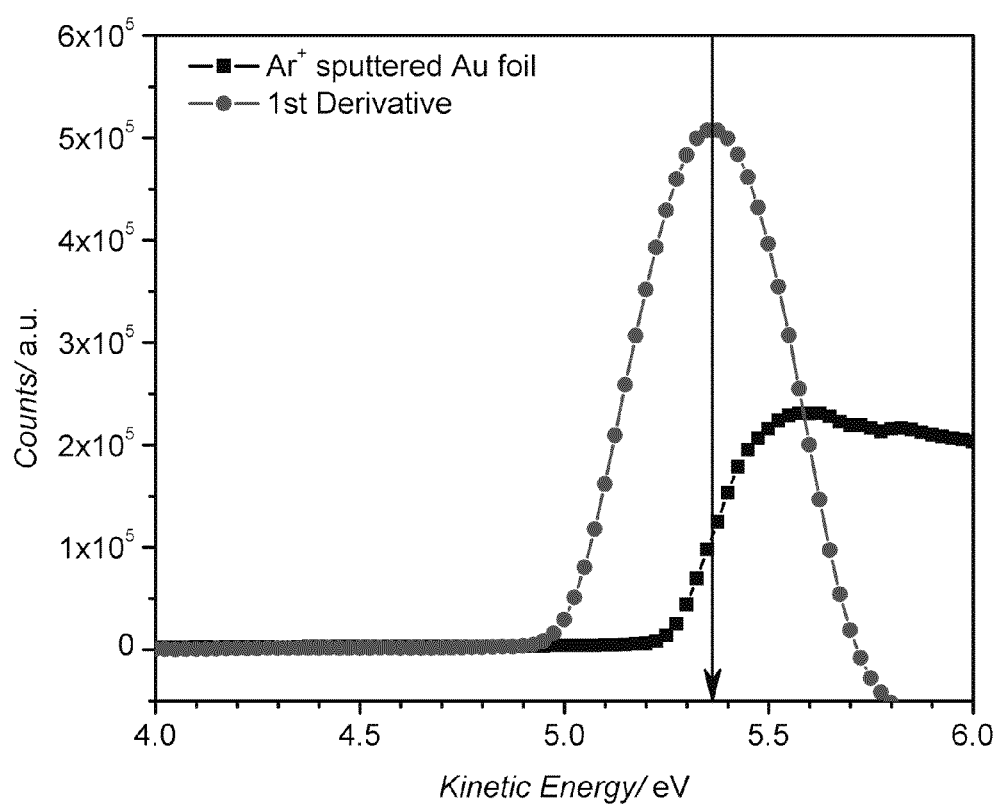
FIG. 11 is a secondary electron cutoff spectrum and first derivative of $Ar^+$ ion sputter-cleaned Au foil represented on the kinetic energy scale. The vertical line through the center of the first derivative is a guide for reading the work function directly from the kinetic energy scale.

Work function values were obtained following a modified method previously described (M. M. Beerbom et al., *Journal of Electron Spectroscopy and Related Phenomena* 152, 2006, 12-17). The spectrometer's analyzer was calibrated according to the manufacturer's guidelines to yield photoemission lines of Ar$^+$ ion sputter-cleaned Cu and Au foils for Cu 2p 3/2 and Au 4f 7/2 at 932.62 eV and 83.96 eV, respectively, following ISO 15472 (M. P. Seah, *Surf Interface Anal.*, 31, 2001, 721-723). This procedure ensures the linearity of the binding energy scale for the instrument, extrapolated out to the secondary electron cutoff (SEC) near the photon energy of the system (1486.6 eV for monochromated Al K-α x-rays). SEC spectra were measured at an x-ray power of 25 W and 15 kV acceleration at normal emission. For all SEC spectra a bias of −15V was applied during measurement to ensure sufficient separation of the sample SEC and that of the analyzer. Under these conditions a SEC value of 1466.24 eV for clean, polycrystalline gold was obtained, corresponding to a work function of 5.36 eV. Because the Cu and Au core level spectra mentioned above are referenced to the Fermi level, set at zero binding energy, the work function of Au was obtained by $\Phi_{Au}$=(hv−q$V_{app}$−$E_{SEC}$) where hv is the x-ray photon energy, $V_{app}$ is the applied bias and $E_{SEC}$ is the position of the secondary electron cutoff on the binding energy scale. Ideally, the SEC edge should be a step function at 0 K, however experimental conditions include thermal and instrumental broadening. Hence, the position of the SEC is taken as the local maximum of the first derivative of the SEC feature. FIG. 11 shows the SEC spectrum of clean, polycrystalline Au foil and its corresponding first derivative. Once the work function of clean Au has been obtained thusly, all other sample work functions can be derived simply from their SEC positions obtained via the first derivative method as $\Phi_{sample}$=($E_{SEC,Au}$−$E_{SEC,sample}$)+$\Phi_{Au}$. FIGS. 12A-12C show the SEC spectra for Al, Ag, and Cu with and without $C_{60}$-bis. FIG. 14C includes the SEC spectrum of clean Au foil as a reference.

While illustrative embodiments have been illustrated and described, it will be appreciated that various changes can be made therein without departing from the spirit and scope of the invention.

The embodiments of the invention in which an exclusive property or privilege is claimed are defined as follows:

1. A fullerene compound, comprising:
   (a) a fullerene group;
   (b) one or more cationic nitrogen centers covalently coupled to the fullerene group;
   (c) one or more hydrophilic groups covalently coupled to the fullerene group; and
   (d) one or more counter ions associated with the cationic nitrogen center, wherein the compound has the structure:

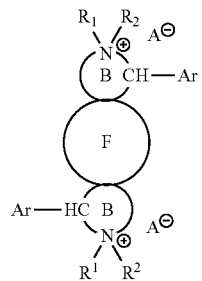

wherein F is a fullerene group;

B is a N-containing ring having from 5-7 ring atoms;

$R_1$ and $R_2$ are independently selected from the group consisting of a polyalkylene oxide and a C1-C20 alkyl optionally substituted with an anionic center;

Ar is —$C_6H_5$-PEO, wherein —$C_6H_5$-PEO is selected from the group consisting of mono-, di-, tri-, and tetra-PEO substituted phenyl, and wherein PEO is a polyethylene oxide; and $A^-$ is a counter ion associated with the cationic nitrogen center.

2. The compound of claim 1, wherein the fullerene group is selected from the group consisting of $C_{60}$, $C_{70}$, $C_{76}$, $C_{78}$, $C_{82}$, $C_{84}$, and $C_{92}$ fullerene groups.

3. The compound of claim 1, wherein the polyalkene oxide group is a polyethylene oxide group having the formula —$(CH_2CH_2O)_n$—, where n is from 1 to about 20.

4. The compound of claim 1 further comprising an anionic center.

5. The compound of claim 4, wherein the anionic center is selected from the group consisting of sulfonate ($SO_3^{2-}$) and carboxylate (—$CO_2^-$) groups.

6. The compound of claim 1, wherein the compound is a bis-fulleropyrrolidium compound.

7. The compound of claim 1 having the structure:

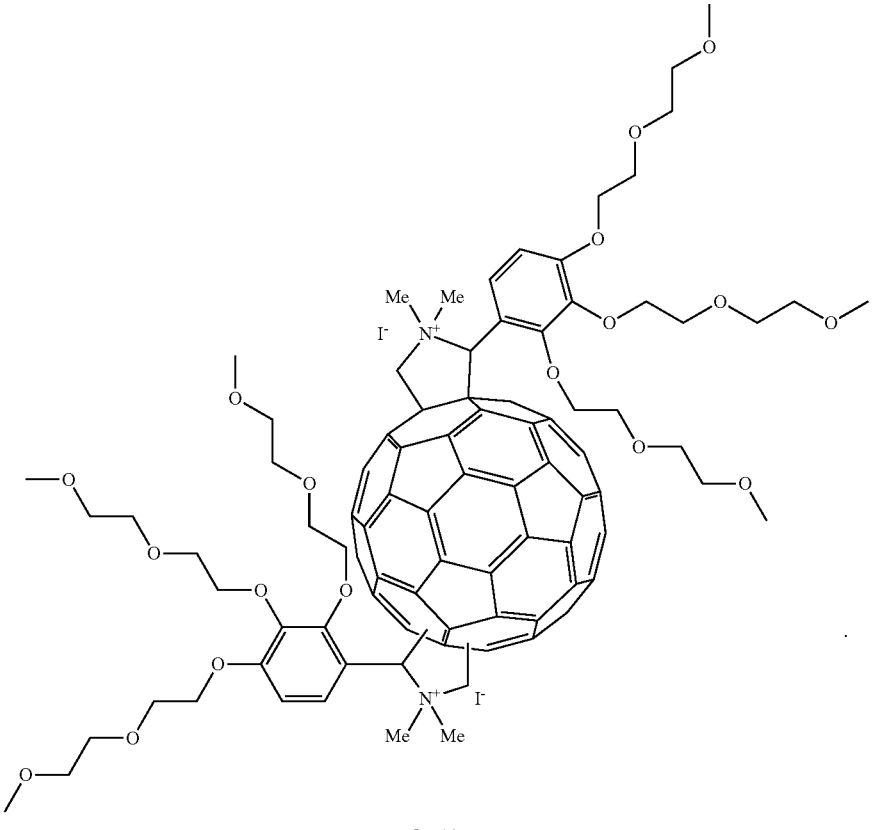

$C_{60}$-bis

8. A photovoltaic device, comprising an interfacial layer intermediate the cathode and active layer, the interfacial layer comprising a compound of claim 1.

9. A photovoltaic device comprising:
(a) a first electrode;
(b) an active layer disposed on a surface of the first electrode;
(c) a layer comprising a compound of claim 1 disposed on a surface of the active layer opposite the first electrode; and
(d) a second electrode disposed on a surface of the layer comprising a compound of claim 1 opposite the active layer.

10. The device of claim 9 further comprising a charge transport layer intermediate the first electrode and the active layer.

11. The device of claim 9, wherein the active layer comprises an active fullerene material.

12. The compound of claim 1 having the structure:

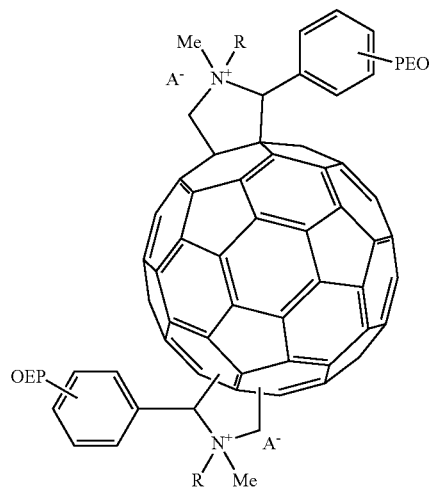

F2 wherein
R is independently selected from the group consisting of C1-C20 straight chain and branched alkyl;
PEO is an alkylene oxide group independently selected from the group consisting of polyethylene oxide having the formula —$(CH_2CH_2O)_n$—, where n is from 1 to about 20 or polypropylene oxide having the formula —$(CH(CH_3)CH_2O)_n$—, where n is from 1 to about 20;
$C_6H_5$-PEO is selected from the group consisting of mono-, di-, tri-, and tetra-PEO substituted phenyl; and
$A^-$ is a counter ion selected from the group consisting of fluoride, chloride, bromide, iodide, trifluoromethyl sulfonyl ($CF_3SO_3^-$), tetrakis(imidazolyl)borate ($BIm_4^-$), and tetrakis(3,5-bis(trifluoromethyl)phenyl]borate ($TFPB^-$).

13. The compound of claim 1 having the structure:

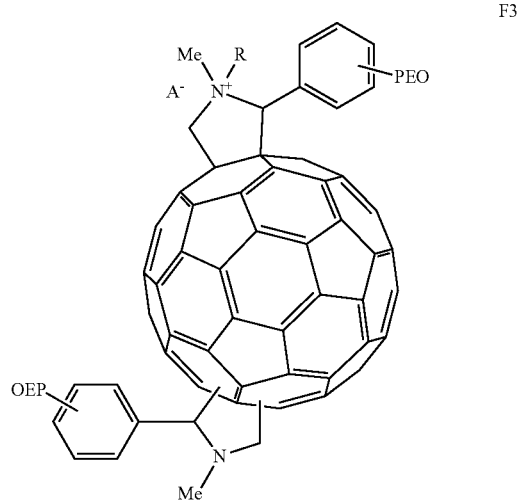

F3 wherein
R is independently selected from the group consisting of C1-C20 straight chain and branched alkyl;
PEO is an alkylene oxide group independently selected from the group consisting of polyethylene oxide having the formula —$(CH_2CH_2O)_n$—, where n is from 1 to about 20 or polypropylene oxide having the formula —$(CH(CH_3)CH_2O)_n$—, where n is from 1 to about 20;
$C_6H_5$-PEO is selected from the group consisting of mono-, di-, tri-, and tetra-PEO substituted phenyl; and
$A^-$ is a counter ion selected from the group consisting of fluoride, chloride, bromide, iodide, trifluoromethyl sulfonyl ($CF_3SO_3^-$), tetrakis(imidazolyl)borate ($BIm_4^-$), and tetrakis(3,5-bis(trifluoromethyl)phenyl]borate ($TFPB^-$).

* * * * *